US009775898B2

(12) United States Patent
Wu et al.

(10) Patent No.: US 9,775,898 B2
(45) Date of Patent: Oct. 3, 2017

(54) VACCINE COMPOSITION COMPRISING AN IMMUNOGENIC PROTEIN AND COMBINATION ADJUVANTS FOR USE IN ELICITING ANTIGEN-SPECIFIC T-CELL RESPONSES

(71) Applicant: TheVax Genetics Vaccine Co., Ltd., Taipei (TW)

(72) Inventors: Chia-Mao Wu, Hsinchu County (TW); Jiun-Ming Wu, Hsinchu County (TW); Yi-Tsui Chiu, Hsinchu County (TW); Yin-Ching Lin, Hsinchu County (TW); Hsien-Kai Chuang, Hsinchu County (TW); Fu-Tan Hsieh, Hsinchu County (TW); Kuan-Ming Chen, Hsinchu County (TW)

(73) Assignee: TheVax Genetics Vaccine Co., Ltd., Taipei (TW)

( * ) Notice: Subject to any disclaimer, the term of this patent is extended or adjusted under 35 U.S.C. 154(b) by 0 days.

(21) Appl. No.: 15/052,713

(22) Filed: Feb. 24, 2016

(65) Prior Publication Data
US 2016/0250324 A1 Sep. 1, 2016

Related U.S. Application Data

(60) Provisional application No. 62/121,406, filed on Feb. 26, 2015.

(51) Int. Cl.
A61K 39/39 (2006.01)
A61K 38/16 (2006.01)
A61K 38/17 (2006.01)
A61K 39/12 (2006.01)
C12N 7/00 (2006.01)
A61K 39/00 (2006.01)

(52) U.S. Cl.
CPC ............ A61K 39/39 (2013.01); A61K 38/164 (2013.01); A61K 38/1774 (2013.01); A61K 39/12 (2013.01); C12N 7/00 (2013.01); A61K 2039/545 (2013.01); A61K 2039/55511 (2013.01); A61K 2039/55561 (2013.01); A61K 2039/55572 (2013.01); A61K 2039/55577 (2013.01); A61K 2039/585 (2013.01); A61K 2039/6031 (2013.01); A61K 2039/6037 (2013.01); C12N 2710/20033 (2013.01); C12N 2710/20034 (2013.01); C12N 2710/20071 (2013.01)

(58) Field of Classification Search
None
See application file for complete search history.

(56) References Cited

U.S. PATENT DOCUMENTS

| | | | | |
|---|---|---|---|---|
| 5,686,281 A | * | 11/1997 | Roberts ................. | C07K 14/55 435/456 |
| 7,736,658 B2 | * | 6/2010 | Dominowski ..... | A61K 39/0225 424/184.1 |
| 8,722,053 B2 | | 5/2014 | Champion et al. | |
| 8,846,080 B2 | | 9/2014 | Biemans et al. | |
| 9,339,536 B2 | * | 5/2016 | Chou ..................... | A61K 39/21 |
| 9,481,714 B2 | * | 11/2016 | Wu ........................ | A61K 39/21 |
| 2006/0217298 A1 | | 9/2006 | Srivastava et al. | |
| 2012/0093821 A1 | * | 4/2012 | Roden ................... | A61K 38/16 424/139.1 |
| 2013/0156859 A1 | | 6/2013 | Koshi et al. | |
| 2014/0154280 A1 | | 6/2014 | Chou et al. | |
| 2014/0154285 A1 | | 6/2014 | Wu et al. | |

FOREIGN PATENT DOCUMENTS

| | | | |
|---|---|---|---|
| EP | 2078726 | * | 7/2009 |
| WO | WO 2004/087196 | * | 10/2004 |
| WO | WO 2008/036682 | * | 3/2008 |
| WO | WO 2011/161260 | * | 12/2011 |
| WO | 2015002954 A1 | | 1/2015 |

OTHER PUBLICATIONS

Sequence alignment of SEQ ID No. 44 with Geneseq database access No. ARL60619 in WO 2007071962 by Monczuk et al. on May 15, 2008.*
Sequence alignment of SEQ ID No. 45 with Geneseq database access No. ADC22488 in WO 2003012068 by Bright et al. on Dec. 18, 2003.*
(Petrovsky et al.)Carbohydrate-based immune adjuvants. Expert Rev Vaccines. Apr. 30, 2011 (Apr. 30, 2011) vol. 10 issue 4 pp. 523-537. author manuscript pp. 1-23, p. 10 Para 2. p. 11 para 1.

* cited by examiner

Primary Examiner — Shanon A Foley
(74) Attorney, Agent, or Firm — Hsiu-Ming Saunders; Intellectual Property Connections, Inc.

(57) ABSTRACT

Vaccine compositions for use in inducing enhanced antigen-specific T cell-mediated immune responses in a subject in need thereof are disclosed. The composition comprises (a) a therapeutically effective amount of an immunogenic protein comprising at least an antigen of a pathogen; (b) a saponin-base adjuvant selected from the group consisting of GPI-0100, Quil A, QS-21; and (c) a Toll-like receptor (TLR) agonist adjuvant selected from the group consisting of monophosphoryl lipid A (MPL), and CpG1826.

19 Claims, 6 Drawing Sheets

Figure 5A:
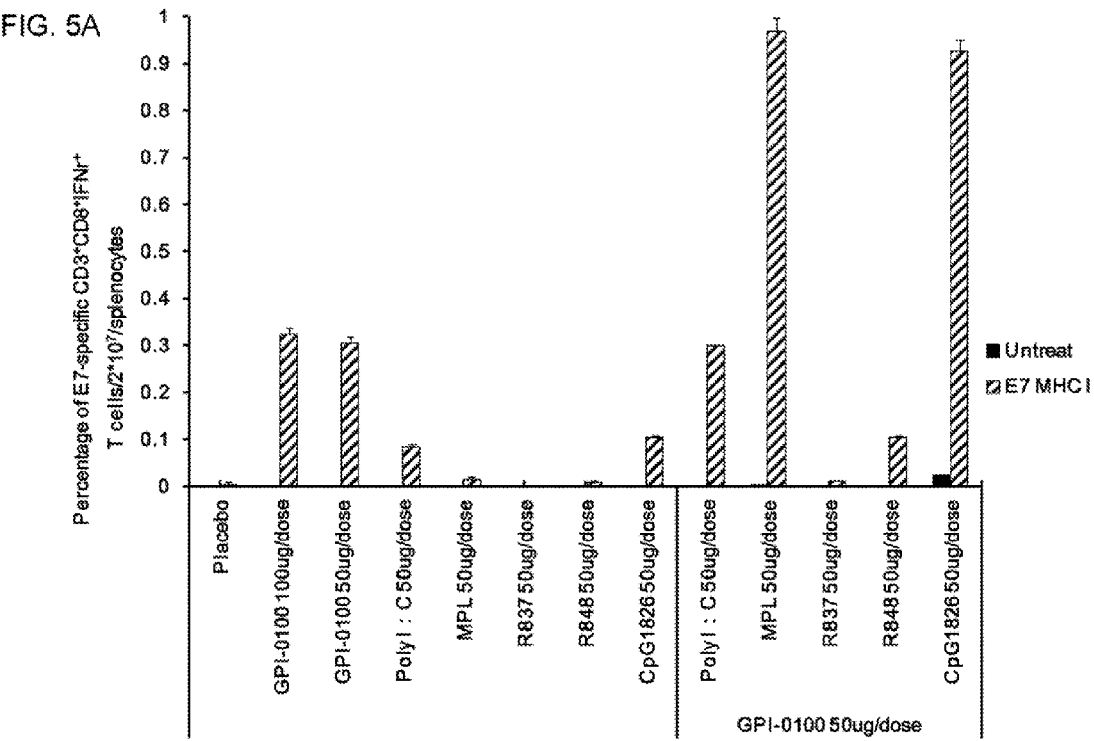

FIG. 1
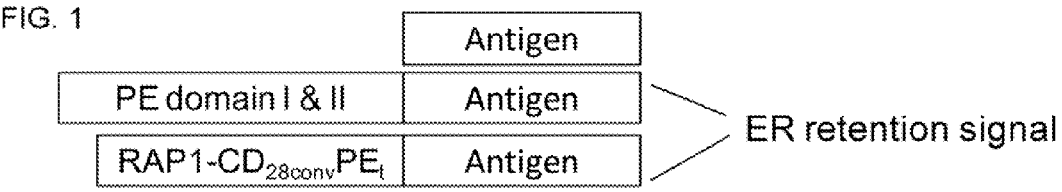
FIG. 2
cell-mediated immunogenicity
| Adjuvant \ Immunogenic protein | E7 | PE$_{407}$-E7-K3 | RAP1-CD$_{28conv}$PE$_t$-E7-K3 |
|---|---|---|---|
| Alum | - | - | ++ |
| GPI-0100 | + | +++ | ++++ |
| QS-21 | + | +++ | ++++ |
-: negative, +: weak, ++: medium, +++: strong, ++++: very strong
FIG. 3
Humoral immunogenicity
| Adjuvant \ Immunogenic protein | E7 | PE$_{407}$-E7-K3 | RAP1-CD$_{28conv}$PE$_t$-E7-K3 |
|---|---|---|---|
| Alum | ++ | ++ | ++ |
| GPI-0100 | ++ | +++ | +++ |
| QS-21 | ++ | +++ | +++ |
-: negative, +: weak, ++: medium, +++: strong
FIG. 4
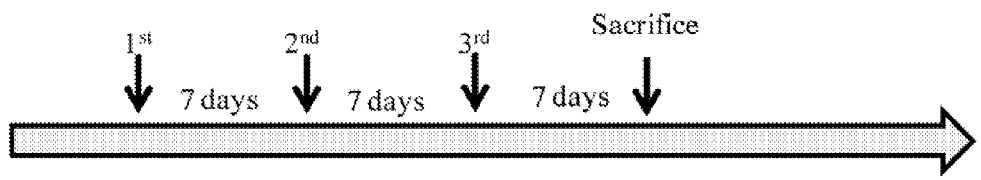

FIG. 7A
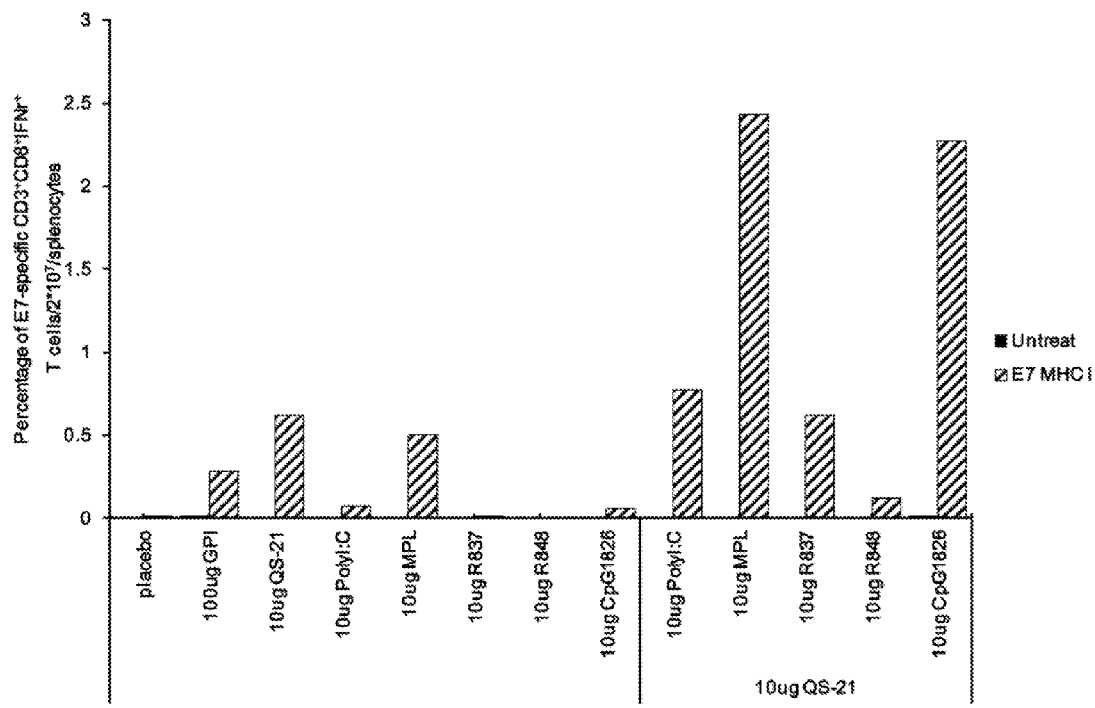
FIG. 10A
| Formulation No. | Protein | QS-21 | GPI-0100 | MPL | CpG1826 |
|---|---|---|---|---|---|
| A | | placebo | | | |
| B | | | 100 μg | | |
| C | | 10 μg | | | |
| D | PE$_{407}$-E7-K3 | | 50 μg | | |
| E | | 10 μg | | 10 μg | |
| F | | 10 μg | | | 10 μg |
| G | | | 50 μg | 50 μg | |
| H | | | 50 μg | | 50 μg |
FIG. 10B
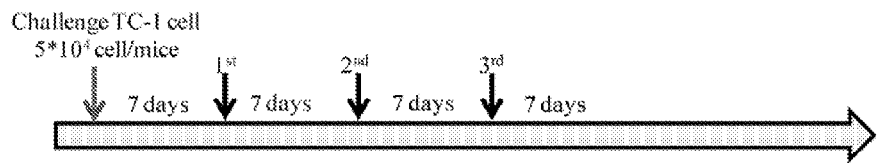

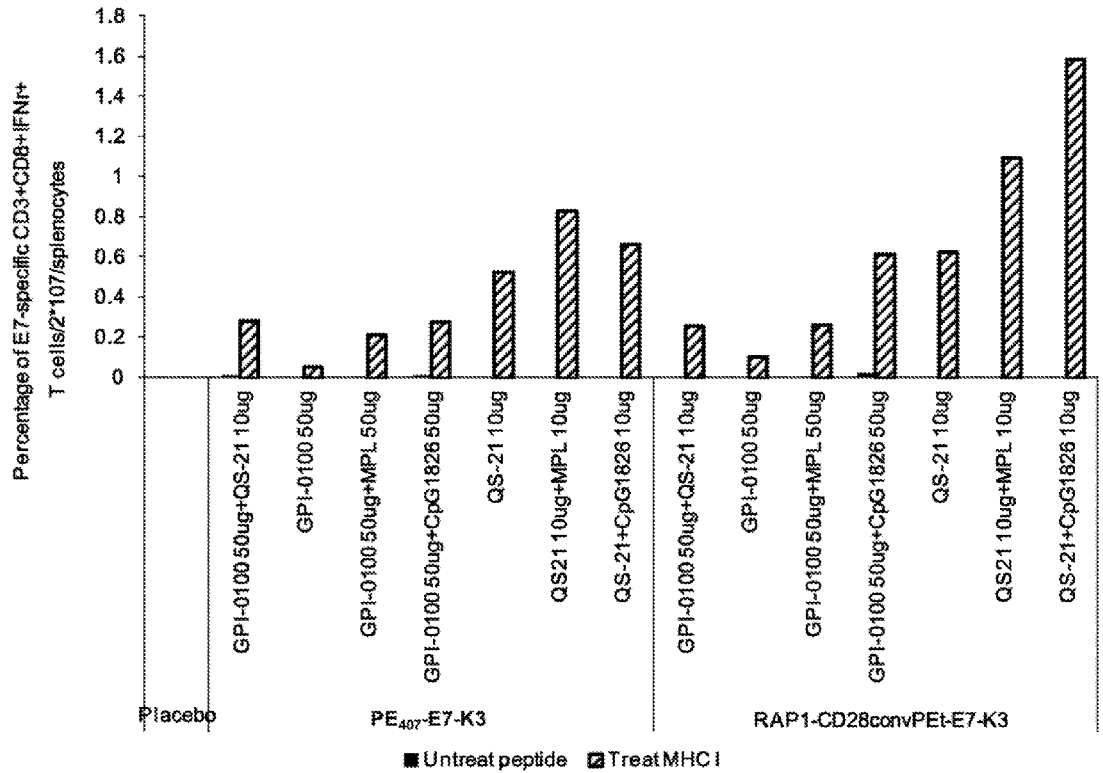
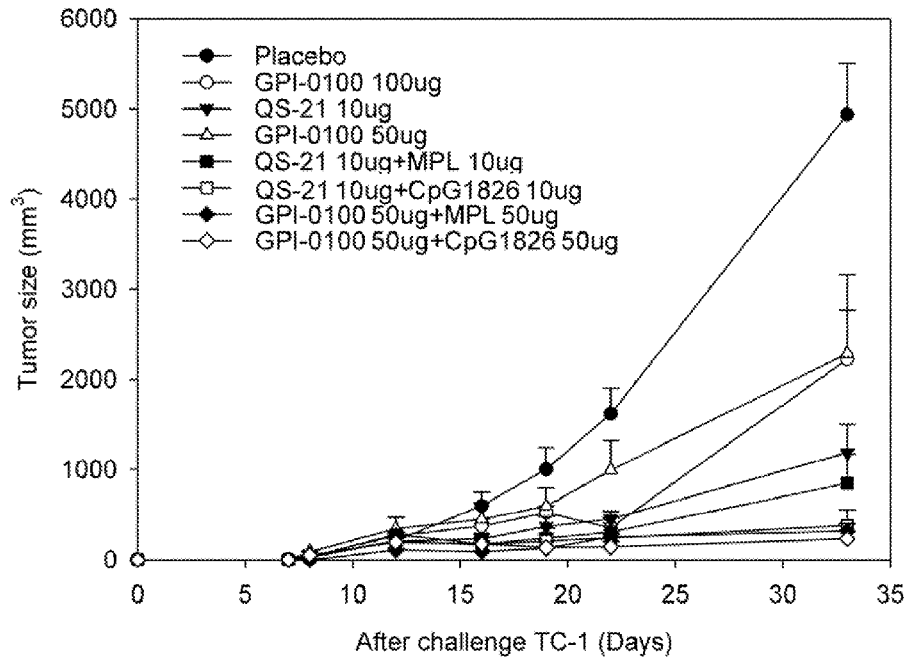

SEQUENCE LISTING

<160> NUMBER OF SEQ ID NOS: 55

<210> SEQ ID NO 1
<211> LENGTH: 28
<212> TYPE: PRT
<213> ORGANISM: Artificial Sequence
<220> FEATURE:
<223> OTHER INFORMATION: hCD28 Core

<400> SEQUENCE: 1

Thr Asp Ile Tyr Phe Cys Lys Ile Glu Val Met Tyr Pro Pro Tyr
1               5                   10                  15

Leu Asp Asn Glu Lys Ser Asn Gly Thr Ile Ile His
            20                  25

<210> SEQ ID NO 2
<211> LENGTH: 53
<212> TYPE: PRT
<213> ORGANISM: Artificial Sequence
<220> FEATURE:
<223> OTHER INFORMATION: hCD28 Maximum

<400> SEQUENCE: 2

Asn Cys Asp Gly Lys Leu Gly Asn Glu Ser Val Thr Phe Tyr Leu Gln
1               5                   10                  15

Asn Leu Tyr Val Asn Gln Thr Asp Ile Tyr Phe Cys Lys Ile Glu Val
            20                  25                  30

Met Tyr Pro Pro Tyr Leu Asp Asn Glu Lys Ser Asn Gly Thr Ile
        35                  40                  45

Ile His Val Lys Gly
    50

<210> SEQ ID NO 3
<211> LENGTH: 34
<212> TYPE: PRT
<213> ORGANISM: Artificial Sequence
<220> FEATURE:
<223> OTHER INFORMATION: PEt Core

<400> SEQUENCE: 3

Gly Trp Glu Gln Leu Glu Gln Cys Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg

<210> SEQ ID NO 4
<211> LENGTH: 112
<212> TYPE: PRT
<213> ORGANISM: Artificial Sequence
<220> FEATURE:
<223> OTHER INFORMATION: PEt Maximum

<400> SEQUENCE: 4

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
            100                 105                 110

<210> SEQ ID NO 5
<211> LENGTH: 104
<212> TYPE: PRT
<213> ORGANISM: Artificial Sequence
<220> FEATURE:
<223> OTHER INFORMATION: RAP1 Minimum

<400> SEQUENCE: 5

Ala Glu Phe Glu Glu Pro Arg Val Ile Asp Leu Trp Asp Leu Ala Gln
1               5                   10                  15

Ser Ala Asn Leu Thr Asp Lys Glu Leu Glu Ala Phe Arg Glu Glu Leu
                20                  25                  30

Lys His Phe Glu Ala Lys Ile Glu Lys His Asn His Tyr Gln Lys Gln
            35                  40                  45

Leu Glu Ile Ala His Glu Lys Leu Arg His Ala Glu Ser Val Gly Asp
    50                  55                  60

Gly Glu Arg Val Ser Arg Ser Glu Lys His Ala Leu Leu Glu Gly
65                  70                  75                  80

Arg Thr Lys Glu Leu Gly Tyr Thr Val Lys Lys His Leu Gln Asp Leu
                85                  90                  95

Ser Gly Arg Ile Ser Arg Ala Arg
            100

<210> SEQ ID NO 6
<211> LENGTH: 153
<212> TYPE: PRT
<213> ORGANISM: Artificial Sequence
<220> FEATURE:
<223> OTHER INFORMATION: A2M Minimum

<400> SEQUENCE: 6

Val Tyr Leu Gln Thr Ser Leu Lys Tyr Asn Ile Leu Pro Glu Lys Glu
1               5                   10                  15

Glu Phe Pro Phe Ala Leu Gly Val Gln Thr Leu Pro Gln Thr Cys Asp
                20                  25                  30

Glu Pro Lys Ala His Thr Ser Phe Gln Ile Ser Leu Ser Val Ser Tyr
            35                  40                  45

Thr Gly Ser Arg Ser Ala Ser Asn Met Ala Ile Val Asp Val Lys Met
    50                  55                  60

Val Ser Gly Phe Ile Pro Leu Lys Pro Thr Val Lys Met Leu Glu Arg
65                  70                  75                  80

Ser Asn His Val Ser Arg Thr Glu Val Ser Ser Asn His Val Leu Ile
                85                  90                  95

Tyr Leu Asp Lys Val Ser Asn Gln Thr Leu Ser Leu Phe Phe Thr Val
            100                 105                 110

Leu Gln Asp Val Pro Val Arg Asp Leu Lys Pro Ala Ile Val Lys Val
        115                 120                 125

Tyr Asp Tyr Tyr Glu Thr Asp Glu Phe Ala Ile Ala Glu Tyr Asn Ala
    130                 135                 140

Pro Cys Ser Lys Asp Leu Gly Asn Ala

<210> SEQ ID NO 7
<211> LENGTH: 24
<212> TYPE: PRT
<213> ORGANISM: Artificial Sequence
<220> FEATURE:
<223> OTHER INFORMATION: HIV-Tat Minimum

<400> SEQUENCE: 7

Arg Gly Asp Pro Thr Gly Gln Glu Glu Ser Lys Glu Lys Val Glu Lys
1               5                   10                  15

Glu Thr Val Val Asp Pro Val Thr
            20

<210> SEQ ID NO 8
<211> LENGTH: 641
<212> TYPE: PRT
<213> ORGANISM: Artificial Sequence
<220> FEATURE:
<223> OTHER INFORMATION: HSPs Minimum

<400> SEQUENCE: 8

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

```
Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Lys Tyr Lys Ala Glu
        515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
610                 615                 620

Gln Gly Pro Lys Gly Gly Ser Gly Ser Gly Pro Thr Ile Glu Glu Val
625                 630                 635                 640

Asp

<210> SEQ ID NO 9
<211> LENGTH: 252
<212> TYPE: PRT
<213> ORGANISM: Pseudomonas aeruginosa

<400> SEQUENCE: 9
```

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu
                245                 250
```

<210> SEQ ID NO 10
<211> LENGTH: 613
<212> TYPE: PRT
<213> ORGANISM: Pseudomonas aeruginosa

<400> SEQUENCE: 10

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125
```

```
Met Ser Pro Ile Tyr Thr Ile Glu Met Gly Asp Glu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540
```

```
Pro Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
            565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
            595                 600                 605

Arg Glu Asp Leu Lys
    610

<210> SEQ ID NO 11
<211> LENGTH: 323
<212> TYPE: PRT
<213> ORGANISM: Homo sapiens

<400> SEQUENCE: 11

Tyr Ser Arg Glu Lys Asn Gln Pro Lys Pro Ser Pro Lys Arg Glu Ser
1               5                   10                  15

Gly Glu Glu Phe Arg Met Glu Lys Leu Asn Gln Leu Trp Glu Lys Ala
            20                  25                  30

Gln Arg Leu His Leu Pro Pro Val Arg Leu Ala Glu Leu His Ala Asp
        35                  40                  45

Leu Lys Ile Gln Glu Arg Asp Glu Leu Ala Trp Lys Lys Leu Lys Leu
50                  55                  60

Asp Gly Leu Asp Glu Asp Gly Glu Lys Glu Ala Arg Leu Ile Arg Asn
65                  70                  75                  80

Leu Asn Val Ile Leu Ala Lys Tyr Gly Leu Asp Gly Lys Lys Asp Ala
                85                  90                  95

Arg Gln Val Thr Ser Asn Ser Leu Ser Gly Thr Gln Glu Asp Gly Leu
            100                 105                 110

Asp Asp Pro Arg Leu Glu Lys Leu Trp His Lys Ala Lys Thr Ser Gly
        115                 120                 125

Lys Phe Ser Gly Glu Glu Leu Asp Lys Leu Trp Arg Glu Phe Leu His
130                 135                 140

His Lys Glu Lys Val His Glu Tyr Asn Val Leu Leu Glu Thr Leu Ser
145                 150                 155                 160

Arg Thr Glu Glu Ile His Glu Asn Val Ile Ser Pro Ser Asp Leu Ser
                165                 170                 175

Asp Ile Lys Gly Ser Val Leu His Ser Arg His Thr Glu Leu Lys Glu
            180                 185                 190

Lys Leu Arg Ser Ile Asn Gln Gly Leu Asp Arg Leu Arg Arg Val Ser
        195                 200                 205

His Gln Gly Tyr Ser Thr Glu Ala Glu Phe Glu Glu Pro Arg Val Ile
    210                 215                 220

Asp Leu Trp Asp Leu Ala Gln Ser Ala Asn Leu Thr Asp Lys Glu Leu
225                 230                 235                 240

Glu Ala Phe Arg Glu Glu Leu Lys His Phe Glu Ala Lys Ile Glu Lys
                245                 250                 255

His Asn His Tyr Gln Lys Gln Leu Glu Ile Ala His Glu Lys Leu Arg
            260                 265                 270

His Ala Glu Ser Val Gly Asp Gly Glu Arg Val Ser Arg Ser Arg Glu
        275                 280                 285

Lys His Ala Leu Leu Glu Gly Arg Thr Lys Glu Leu Gly Tyr Thr Val
    290                 295                 300
```

Lys Lys His Leu Gln Asp Leu Ser Gly Arg Ile Ser Arg Ala Arg His
305                 310                 315                 320

Asn Glu Leu

<210> SEQ ID NO 12
<211> LENGTH: 357
<212> TYPE: PRT
<213> ORGANISM: Homo sapiens

<400> SEQUENCE: 12

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
                20                  25                  30

Gly Lys Tyr Ser Arg Glu Lys Asn Gln Pro Lys Pro Ser Pro Lys Arg
            35                  40                  45

Glu Ser Gly Glu Glu Phe Arg Met Glu Lys Leu Asn Gln Leu Trp Glu
50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
            260                 265                 270

Glu Leu Glu Ala Phe Arg Glu Glu Leu Lys His Phe Glu Ala Lys Ile
        275                 280                 285

Glu Lys His Asn His Tyr Gln Lys Gln Leu Glu Ile Ala His Glu Lys
290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
            340                 345                 350

Arg His Asn Glu Leu
        355

<210> SEQ ID NO 13
<211> LENGTH: 101
<212> TYPE: PRT
<213> ORGANISM: Human immunodeficiency virus

<400> SEQUENCE: 13

Met Glu Pro Val Asp Pro Arg Leu Glu Pro Trp Lys His Pro Gly Ser
1               5                   10                  15

Gln Pro Lys Thr Pro Cys Thr Lys Cys Tyr Cys Lys Cys Cys Leu
            20                  25                  30

His Cys Gln Val Cys Phe Met Thr Lys Gly Leu Gly Ile Ser Tyr Gly
        35                  40                  45

Arg Lys Lys Arg Arg Gln Arg Arg Ala Pro Gln Asp Asn Lys Asn
    50                  55                  60

His Gln Val Ser Leu Ser Lys Gln Pro Thr Ser Arg Ala Arg Gly Asp
65                  70                  75                  80

Pro Thr Gly Gln Glu Glu Ser Lys Glu Lys Val Glu Lys Glu Thr Val
                85                  90                  95

Val Asp Pro Val Thr
            100

<210> SEQ ID NO 14
<211> LENGTH: 4
<212> TYPE: PRT
<213> ORGANISM: Artificial Sequence
<220> FEATURE:
<223> OTHER INFORMATION: ER retention sequence

<400> SEQUENCE: 14

Lys Asp Glu Leu
1

<210> SEQ ID NO 15
<211> LENGTH: 6
<212> TYPE: PRT
<213> ORGANISM: Artificial Sequence
<220> FEATURE:
<223> OTHER INFORMATION: Linker of CD28-PEt
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Arg Xaa Arg Xaa Lys Arg
1               5

<210> SEQ ID NO 16
<211> LENGTH: 12
<212> TYPE: PRT
<213> ORGANISM: Artificial Sequence
<220> FEATURE:
<223> OTHER INFORMATION: ER retention sequence

<400> SEQUENCE: 16

Lys Lys Asp Leu Arg Asp Glu Leu Lys Asp Glu Leu
1               5                   10

<210> SEQ ID NO 17
<211> LENGTH: 13
<212> TYPE: PRT
<213> ORGANISM: Artificial Sequence
<220> FEATURE:
<223> OTHER INFORMATION: ER retention sequence

<400> SEQUENCE: 17

Lys Lys Asp Glu Leu Arg Asp Glu Leu Lys Asp Glu Leu
1               5                   10

<210> SEQ ID NO 18
<211> LENGTH: 13
<212> TYPE: PRT
<213> ORGANISM: Artificial Sequence
<220> FEATURE:
<223> OTHER INFORMATION: ER retention sequence

<400> SEQUENCE: 18

Lys Lys Asp Glu Leu Arg Val Glu Leu Lys Asp Glu Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: ER retention sequence

<400> SEQUENCE: 19

Lys Asp Glu Leu Lys Asp Glu Leu Lys Asp Glu Leu
1               5                   10

<210> SEQ ID NO 20
<211> LENGTH: 46
<212> TYPE: PRT
<213> ORGANISM: Pseudomonas aeruginosa

<400> SEQUENCE: 20

Pro Leu Glu Thr Phe Thr Arg His Arg Gln Pro Arg Gly Trp Glu Gln
1               5                   10                  15

Leu Glu Gln Cys Gly Tyr Pro Val Gln Arg Leu Val Ala Leu Tyr Leu
                20                  25                  30

Ala Ala Arg Leu Ser Trp Asn Gln Val Asp Gln Val Ile Arg
            35                  40                  45

<210> SEQ ID NO 21
<211> LENGTH: 98
<212> TYPE: PRT
<213> ORGANISM: Human papillomavirus type 16

<400> SEQUENCE: 21

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

```
Asp Leu Leu Met Gly Thr Leu Gly Ile Val Cys Pro Ile Cys Ser Gln
            85                  90                  95

Lys Pro

<210> SEQ ID NO 22
<211> LENGTH: 105
<212> TYPE: PRT
<213> ORGANISM: Human papillomavirus type 18

<400> SEQUENCE: 22

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 23
<211> LENGTH: 190
<212> TYPE: PRT
<213> ORGANISM: Hepatitis C virus

<400> SEQUENCE: 23

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Asn Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser
            180                 185                 190
```

<210> SEQ ID NO 24
<211> LENGTH: 154
<212> TYPE: PRT
<213> ORGANISM: Hepatitis B virus

<400> SEQUENCE: 24

```
Met Ala Ala Arg Met Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Ala Leu Pro Pro Ser Ser Ala Ser Ala Val Pro Ala Asp
        35                  40                  45

His Gly Ser His Leu Ser Leu Arg Gly Leu Pro Val Cys Ser Phe Ser
    50                  55                  60

Ser Ala Gly Pro Cys Ala Leu Arg Phe Thr Ser Ala Arg Arg Met Glu
65                  70                  75                  80

Thr Thr Val Asn Ala Pro Trp Ser Leu Pro Thr Val Leu His Lys Arg
                85                  90                  95

Thr Ile Gly Leu Ser Gly Arg Ser Met Thr Trp Ile Glu Glu Tyr Ile
            100                 105                 110

Lys Asp Cys Val Phe Lys Asp Trp Glu Glu Leu Gly Glu Glu Ile Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150
```

<210> SEQ ID NO 25
<211> LENGTH: 192
<212> TYPE: PRT
<213> ORGANISM: Porcine circovirus

<400> SEQUENCE: 25

```
Asn Gly Ile Phe Asn Thr Arg Leu Ser Arg Thr Phe Gly Tyr Thr Ile
1               5                   10                  15

Lys Arg Thr Thr Val Lys Thr Pro Ser Trp Ala Val Asp Met Met Arg
            20                  25                  30

Phe Asn Ile Asn Asp Phe Leu Pro Pro Gly Gly Gly Ser Asn Pro Arg
        35                  40                  45

Ser Val Pro Phe Glu Tyr Tyr Ser Ile Ser Lys Val Lys Val Glu Phe
    50                  55                  60

Trp Pro Cys Ser Pro Ile Thr Gln Gly Asp Ser Gly Val Gly Ser Ser
65                  70                  75                  80

Ala Val Ile Leu Asp Asp Asn Phe Val Thr Lys Ala Thr Ala Leu Thr
                85                  90                  95

Tyr Asp Pro Tyr Val Asn Tyr Ser Ser Arg His Thr Ile Thr Gln Pro
            100                 105                 110

Phe Ser Tyr His Ser Arg Tyr Phe Thr Pro Lys Pro Val Leu Asp Ser
        115                 120                 125

Thr Ile Asp Tyr Phe Gln Pro Asn Asn Lys Arg Asn Gln Leu Trp Leu
    130                 135                 140

Arg Leu Gln Thr Ala Gly Asn Val Asp His Val Gly Leu Gly Thr Ala
145                 150                 155                 160

Phe Glu Asn Ser Ile Tyr Asp Gln Glu Tyr Asn Ile Arg Val Thr Met
                165                 170                 175
```

```
Tyr Val Gln Phe Arg Glu Phe Asn Leu Lys Asp Pro Pro Leu Asn Pro
            180                 185                 190

<210> SEQ ID NO 26
<211> LENGTH: 220
<212> TYPE: PRT
<213> ORGANISM: Porcine reproductive and respiratory syndrome virus

<400> SEQUENCE: 26

Arg His His Phe Thr Pro Ser Glu Arg Gln Leu Cys Leu Ser Ser Ile
1               5                   10                  15

Gln Thr Ala Phe Asn Gln Gly Ala Gly Thr Cys Ile Leu Ser Asp Ser
            20                  25                  30

Gly Arg Ile Ser Tyr Thr Val Glu Phe Ser Leu Pro Thr His His Thr
        35                  40                  45

Val Arg Leu Ile Arg Val Thr Ala Pro Pro Ser Ala Leu Asp Gln Val
    50                  55                  60

Ile Arg Asn Ala Leu Ala Ser Pro Gly Ser Gly Gly Asp Leu Gly Glu
65                  70                  75                  80

Ala Ile Arg Glu Gln Pro Glu Gln Ala Arg Leu Ala Leu Thr Leu Ala
                85                  90                  95

Ala Ala Glu Ser Glu Arg Phe Val Arg Gln Gly Thr Gly Asn Asp Glu
            100                 105                 110

Ala Gly Ala Ala Asn Ala Asp Val Val Ser Leu Thr Cys Pro Val Ala
        115                 120                 125

Ala Gly Glu Cys Ala Gly Pro Ala Asp Ser Gly Asp Ala Leu Leu Glu
    130                 135                 140

Arg Asn Tyr Pro Thr Gly Ala Glu Phe Leu Gly Asp Gly Gly Asp Val
145                 150                 155                 160

Arg His His Phe Thr Pro Ser Glu Arg Gln Leu Cys Leu Ser Ser Ile
                165                 170                 175

Gln Thr Ala Phe Asn Gln Gly Ala Gly Thr Cys Ile Leu Ser Asp Ser
            180                 185                 190

Gly Arg Ile Ser Tyr Thr Val Glu Phe Ser Leu Pro Thr His His Thr
        195                 200                 205

Val Arg Leu Ile Arg Val Thr Ala Pro Pro Ser Ala
    210                 215                 220

<210> SEQ ID NO 27
<211> LENGTH: 165
<212> TYPE: PRT
<213> ORGANISM: Porcine reproductive and respiratory syndrome virus

<400> SEQUENCE: 27

Asn Asn Lys Glu Cys Thr Val Ala Gln Ala Leu Gly Asn Gly Asp Lys
1               5                   10                  15

Phe Arg Ala Thr Asp Lys Arg Val Val Asp Ser Leu Arg Ala Ile Cys
            20                  25                  30

Ala Asp Leu Glu Gly Ser Ser Ser Pro Leu Pro Lys Val Ala His Asn
        35                  40                  45

Leu Gly Phe Tyr Phe Ser Pro Asp Leu Thr Gln Phe Ala Lys Leu Pro
    50                  55                  60

Ile Glu Leu Asp Pro His Trp Pro Val Val Ser Thr Gln Asn Asn Glu
65                  70                  75                  80

Lys Trp Pro Asp Arg Leu Val Ala Ser Leu Arg Pro Leu Asp Lys Tyr
                85                  90                  95
```

```
Ser Arg Ala Cys Ile Gly Ala Gly Tyr Met Val Gly Pro Ser Val Phe
                100                 105                 110

Leu Gly Thr Pro Gly Val Val Ser Tyr Tyr Leu Thr Lys Phe Val Lys
            115                 120                 125

Gly Glu Ala Gln Val Leu Pro Glu Thr Val Phe Ser Thr Gly Arg Ile
        130                 135                 140

Glu Val Asp Cys Arg Glu Tyr Leu Asp Asp Arg Glu Arg Glu Val Ala
145                 150                 155                 160

Ala Ser Leu Pro His
                165

<210> SEQ ID NO 28
<211> LENGTH: 58
<212> TYPE: PRT
<213> ORGANISM: Porcine reproductive and respiratory syndrome virus

<400> SEQUENCE: 28

Gly Ser Ser Leu Asp Asp Phe Cys Tyr Asp Ser Thr Ala Pro Gln Lys
1               5                   10                  15

Val Leu Leu Ala Phe Ser Ile Thr Tyr Ala Ser Asn Asp Ser Ser Ser
            20                  25                  30

His Leu Gln Leu Ile Tyr Asn Leu Thr Leu Cys Glu Leu Asn Gly Thr
        35                  40                  45

Asp Trp Leu Ala Asn Lys Phe Asp Trp Ala
    50                  55

<210> SEQ ID NO 29
<211> LENGTH: 62
<212> TYPE: PRT
<213> ORGANISM: Porcine reproductive and respiratory syndrome virus

<400> SEQUENCE: 29

Met Gly Ser Leu Asp Asp Phe Cys Asn Asp Ser Thr Ala Ala Gln Lys
1               5                   10                  15

Leu Val Leu Ala Phe Ser Ile Thr Tyr Thr Pro Ile Phe Val Ala Gly
            20                  25                  30

Gly Ser Ser Ser Thr Tyr Gln Tyr Ile Tyr Asn Leu Thr Ile Cys Glu
        35                  40                  45

Leu Asn Gly Thr Asp Trp Leu Ser Asn His Phe Asp Trp Ala
    50                  55                  60

<210> SEQ ID NO 30
<211> LENGTH: 68
<212> TYPE: PRT
<213> ORGANISM: Artificial Sequence
<220> FEATURE:
<223> OTHER INFORMATION: CD28-PEt
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
```

```
<221> NAME/KEY: misc_feature
<222> LOCATION: (32)..(32)
<223> OTHER INFORMATION: Xaa can be any naturally occurring amino acid

<400> SEQUENCE: 30

Thr Asp Ile Tyr Phe Cys Lys Xaa Glu Xaa Xaa Tyr Pro Pro Pro Tyr
1               5                   10                  15

Xaa Asp Asn Glu Lys Ser Asn Gly Thr Ile Ile His Arg Xaa Arg Xaa
            20                  25                  30

Lys Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60

Gln Val Ile Arg
65

<210> SEQ ID NO 31
<211> LENGTH: 28
<212> TYPE: PRT
<213> ORGANISM: Artificial Sequence
<220> FEATURE:
<223> OTHER INFORMATION: CD28 consensus sequence
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 31

Thr Asp Ile Tyr Phe Cys Lys Xaa Glu Xaa Xaa Tyr Pro Pro Pro Tyr
1               5                   10                  15

Xaa Asp Asn Glu Lys Ser Asn Gly Thr Ile Ile His
            20                  25

<210> SEQ ID NO 32
<211> LENGTH: 10
<212> TYPE: PRT
<213> ORGANISM: Artificial Sequence
<220> FEATURE:
<223> OTHER INFORMATION: CD28 critical region
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 32

Lys Xaa Glu Xaa Xaa Tyr Pro Pro Pro Tyr
1               5                   10

<210> SEQ ID NO 33
<211> LENGTH: 187
<212> TYPE: PRT
<213> ORGANISM: Homo sapiens

<400> SEQUENCE: 33

Met Asn Gly Asp Asp Ala Phe Ala Arg Arg Pro Thr Val Gly Ala Gln
```

```
  1               5                  10                 15
Ile Pro Glu Lys Ile Gln Lys Ala Phe Asp Asp Ile Ala Lys Tyr Phe
            20                 25                 30

Ser Lys Glu Glu Trp Glu Lys Met Lys Ala Ser Glu Lys Ile Phe Tyr
            35                 40                 45

Val Tyr Met Lys Arg Lys Tyr Glu Ala Met Thr Lys Leu Gly Phe Lys
     50                 55                 60

Ala Thr Leu Pro Pro Phe Met Cys Asn Lys Arg Ala Glu Asp Phe Gln
 65                 70                 75                 80

Gly Asn Asp Leu Asp Asn Asp Pro Asn Arg Gly Asn Gln Val Glu Arg
            85                 90                 95

Pro Gln Met Thr Phe Gly Arg Leu Gln Gly Ile Ser Pro Lys Ile Met
            100                105                110

Pro Lys Lys Pro Ala Glu Glu Gly Asn Asp Ser Glu Glu Val Pro Glu
            115                120                125

Ala Ser Gly Pro Gln Asn Asp Gly Lys Glu Leu Cys Pro Pro Gly Lys
       130                135                140

Pro Thr Thr Ser Glu Lys Ile His Glu Arg Ser Gly Pro Lys Arg Gly
145                 150                155                160

Glu His Ala Trp Thr His Arg Leu Arg Glu Arg Lys Gln Leu Val Ile
                    165                170                175

Tyr Glu Glu Ile Ser Asp Pro Glu Glu Asp Asp
            180                185

<210> SEQ ID NO 34
<211> LENGTH: 314
<212> TYPE: PRT
<213> ORGANISM: Homo sapiens

<400> SEQUENCE: 34

Met Pro Leu Glu Gln Arg Ser Gln His Cys Lys Pro Glu Glu Gly Leu
 1               5                  10                 15

Glu Ala Arg Gly Glu Ala Leu Gly Leu Val Gly Ala Gln Ala Pro Ala
            20                 25                 30

Thr Glu Glu Gln Glu Ala Ala Ser Ser Ser Ser Thr Leu Val Glu Val
            35                 40                 45

Thr Leu Gly Glu Val Pro Ala Ala Glu Ser Pro Asp Pro Pro Gln Ser
     50                 55                 60

Pro Gln Gly Ala Ser Ser Leu Pro Thr Thr Met Asn Tyr Pro Leu Trp
 65                 70                 75                 80

Ser Gln Ser Tyr Glu Asp Ser Ser Asn Gln Glu Glu Glu Gly Pro Ser
            85                 90                 95

Thr Phe Pro Asp Leu Glu Ser Glu Phe Gln Ala Ala Leu Ser Arg Lys
            100                105                110

Val Ala Glu Leu Val His Phe Leu Leu Leu Lys Tyr Arg Ala Arg Glu
            115                120                125

Pro Val Thr Lys Ala Glu Met Leu Gly Ser Val Val Gly Asn Trp Gln
            130                135                140

Tyr Phe Phe Pro Val Ile Phe Ser Lys Ala Ser Ser Ser Leu Gln Leu
145                 150                155                160

Val Phe Gly Ile Glu Leu Met Glu Val Asp Pro Ile Gly His Leu Tyr
                    165                170                175

Ile Phe Ala Thr Cys Leu Gly Leu Ser Tyr Asp Gly Leu Leu Gly Asp
            180                185                190
```

Asn Gln Ile Met Pro Lys Ala Gly Leu Leu Ile Ile Val Leu Ala Ile
            195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 35
<211> LENGTH: 181
<212> TYPE: PRT
<213> ORGANISM: Homo sapiens

<400> SEQUENCE: 35

Phe Met Gln Ala Glu Gly Arg Gly Thr Gly Gly Ser Thr Gly Asp Ala
1               5                   10                  15

Asp Gly Pro Gly Gly Pro Gly Ile Pro Asp Gly Pro Gly Gly Asn Ala
            20                  25                  30

Gly Gly Pro Gly Glu Ala Gly Ala Thr Gly Gly Arg Gly Pro Arg Gly
        35                  40                  45

Ala Gly Ala Ala Arg Ala Ser Gly Pro Gly Gly Gly Ala Pro Arg Gly
    50                  55                  60

Pro His Gly Gly Ala Ala Ser Gly Leu Asn Gly Cys Cys Arg Cys Gly
65                  70                  75                  80

Ala Arg Gly Pro Glu Ser Arg Leu Leu Glu Phe Tyr Leu Ala Met Pro
                85                  90                  95

Phe Ala Thr Pro Met Glu Ala Glu Leu Ala Arg Arg Ser Leu Ala Gln
            100                 105                 110

Asp Ala Pro Pro Leu Pro Val Pro Gly Val Leu Leu Lys Glu Phe Thr
        115                 120                 125

Val Ser Gly Asn Ile Leu Thr Ile Arg Leu Thr Ala Ala Asp His Arg
130                 135                 140

Gln Leu Gln Leu Ser Ile Ser Ser Cys Leu Gln Gln Leu Ser Leu Leu
145                 150                 155                 160

Met Trp Ile Thr Gln Cys Phe Leu Pro Val Phe Leu Ala Gln Pro Pro
                165                 170                 175

Ser Gly Gln Arg Arg
            180

<210> SEQ ID NO 36
<211> LENGTH: 296
<212> TYPE: PRT
<213> ORGANISM: Homo sapiens

<400> SEQUENCE: 36

Phe Ser Gly Ala Leu Asp Val Leu Gln Met Lys Glu Glu Asp Val Leu
1               5                   10                  15

```
Lys Phe Leu Ala Ala Gly Thr His Leu Gly Thr Asn Leu Asp Phe
             20                  25                  30

Gln Met Glu Gln Tyr Ile Tyr Lys Arg Lys Ser Asp Gly Ile Tyr Ile
         35                  40                  45

Ile Asn Leu Lys Arg Thr Trp Glu Lys Leu Leu Leu Ala Ala Arg Ala
 50                  55                  60

Ile Val Ala Ile Glu Asn Pro Ala Asp Val Ser Val Ile Ser Ser Arg
 65                  70                  75                  80

Asn Thr Gly Gln Arg Ala Val Leu Lys Phe Ala Ala Thr Gly Ala
             85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
            115                 120                 125

Ala Asp His Gln Pro Leu Thr Glu Ala Ser Tyr Val Asn Leu Pro Thr
            130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala Ala His Ser Val Gly Leu Met Trp
                165                 170                 175

Trp Met Leu Ala Arg Glu Val Leu Arg Met Arg Gly Thr Ile Ser Arg
            180                 185                 190

Glu His Pro Trp Glu Val Met Pro Asp Leu Tyr Phe Tyr Arg Asp Pro
            195                 200                 205

Glu Glu Ile Glu Lys Glu Gln Ala Ala Glu Lys Ala Val Thr
210                 215                 220

Lys Glu Glu Phe Gln Gly Glu Trp Thr Ala Pro Ala Pro Glu Phe Thr
225                 230                 235                 240

Ala Thr Gln Pro Glu Val Ala Asp Trp Ser Glu Gly Val Gln Val Pro
            245                 250                 255

Ser Val Pro Ile Gln Gln Phe Pro Thr Glu Asp Trp Ser Ala Gln Pro
            260                 265                 270

Ala Thr Glu Asp Trp Ser Ala Ala Pro Thr Ala Gln Ala Thr Glu Trp
            275                 280                 285

Val Gly Ala Thr Thr Asp Trp Ser
            290                 295

<210> SEQ ID NO 37
<211> LENGTH: 279
<212> TYPE: PRT
<213> ORGANISM: Homo sapiens

<400> SEQUENCE: 37

Gly Ser Asp Val Arg Asp Leu Asn Ala Leu Leu Pro Ala Val Pro Ser
 1               5                  10                  15

Leu Gly Gly Gly Gly Cys Ala Leu Pro Val Ser Gly Ala Ala Gln
             20                  25                  30

Trp Ala Pro Val Leu Asp Phe Ala Pro Gly Ala Ser Ala Tyr Gly
         35                  40                  45

Ser Leu Gly Gly Pro Ala Pro Pro Ala Pro Pro Pro Pro Pro
 50                  55                  60

Pro Pro Pro His Ser Phe Ile Lys Gln Glu Pro Ser Trp Gly Gly Ala
 65                  70                  75                  80

Glu Pro His Glu Glu Gln Cys Leu Ser Ala Phe Thr Val His Phe Ser
             85                  90                  95
```

Gly Gln Phe Thr Gly Thr Ala Gly Ala Cys Arg Tyr Gly Pro Phe Gly
            100                 105                 110

Pro Pro Pro Ser Gln Ala Ser Ser Gly Gln Ala Arg Met Phe Pro
        115                 120                 125

Asn Ala Pro Tyr Leu Pro Ser Cys Leu Glu Ser Gln Pro Ala Ile Arg
130                 135                 140

Asn Gln Gly Tyr Ser Thr Val Thr Phe Asp Gly Thr Pro Ser Tyr Gly
145                 150                 155                 160

His Thr Pro Ser His His Ala Ala Gln Phe Pro Asn His Ser Phe Lys
                165                 170                 175

His Glu Asp Pro Met Gly Gln Gln Gly Ser Leu Gly Glu Gln Gln Tyr
            180                 185                 190

Ser Val Pro Pro Val Tyr Gly Cys His Thr Pro Thr Asp Ser Cys
        195                 200                 205

Thr Gly Ser Gln Ala Leu Leu Leu Arg Thr Pro Tyr Ser Ser Asp Asn
210                 215                 220

Leu Tyr Gln Met Thr Ser Gln Leu Glu Cys Met Thr Trp Asn Gln Met
225                 230                 235                 240

Asn Leu Gly Ala Thr Leu Lys Gly Val Ala Ala Gly Ser Ser Ser Ser
                245                 250                 255

Val Lys Trp Thr Glu Gly Gln Ser Asn His Ser Thr Gly Tyr Glu Ser
            260                 265                 270

Asp Asn His Thr Thr Pro Ile
            275

<210> SEQ ID NO 38
<211> LENGTH: 406
<212> TYPE: PRT
<213> ORGANISM: Homo sapiens

<400> SEQUENCE: 38

Ser Gly Gly His Gln Leu Gln Leu Ala Ala Leu Trp Pro Trp Leu Leu
1               5                   10                  15

Met Ala Thr Leu Gln Ala Gly Phe Gly Arg Thr Gly Leu Val Leu Ala
            20                  25                  30

Ala Ala Val Glu Ser Glu Arg Ser Ala Glu Gln Lys Ala Ile Ile Arg
        35                  40                  45

Val Ile Pro Leu Lys Met Asp Pro Thr Gly Lys Leu Asn Leu Thr Leu
    50                  55                  60

Glu Gly Val Phe Ala Gly Val Ala Glu Ile Thr Pro Ala Glu Gly Lys
65                  70                  75                  80

Leu Met Gln Ser His Pro Leu Tyr Leu Cys Asn Ala Ser Asp Asp Asp
                85                  90                  95

Asn Leu Glu Pro Gly Phe Ile Ser Ile Val Lys Leu Glu Ser Pro Arg
            100                 105                 110

Arg Ala Pro Ala His Pro Leu Ile Cys Gly Pro Pro Gly Leu Asp Lys
        115                 120                 125

Arg Leu Leu Pro Glu Thr Pro Gly Pro Cys Tyr Ser Asn Ser Gln Pro
130                 135                 140

Val Trp Leu Cys Leu Thr Pro Arg Gln Pro Leu Glu Pro His Pro Pro
145                 150                 155                 160

Gly Glu Gly Pro Ser Glu Trp Ser Ser Asp Thr Ala Glu Gly Arg Pro
                165                 170                 175

Cys Pro Tyr Pro His Cys Gln Val Leu Ser Ala Gln Pro Gly Ser Glu

```
                    180                 185                 190
Glu Glu Leu Glu Glu Leu Cys Glu Gln Ala Val Ser Gly Gly His Gln
                195                 200                 205

Leu Gln Leu Ala Ala Leu Trp Pro Trp Leu Leu Met Ala Thr Leu Gln
        210                 215                 220

Ala Gly Phe Gly Arg Thr Gly Leu Val Leu Ala Ala Val Glu Ser
225                 230                 235                 240

Glu Arg Ser Ala Glu Gln Lys Ala Ile Ile Arg Val Ile Pro Leu Lys
                245                 250                 255

Met Asp Pro Thr Gly Lys Leu Asn Leu Thr Leu Glu Gly Val Phe Ala
            260                 265                 270

Gly Val Ala Glu Ile Thr Pro Ala Glu Gly Lys Leu Met Gln Ser His
        275                 280                 285

Pro Leu Tyr Leu Cys Asn Ala Ser Asp Asp Asn Leu Glu Pro Gly
    290                 295                 300

Phe Ile Ser Ile Val Lys Leu Glu Ser Pro Arg Arg Ala Pro Ala His
305                 310                 315                 320

Pro Leu Ile Cys Gly Pro Pro Gly Leu Asp Lys Arg Leu Leu Pro Glu
                325                 330                 335

Thr Pro Gly Pro Cys Tyr Ser Asn Ser Gln Pro Val Trp Leu Cys Leu
            340                 345                 350

Thr Pro Arg Gln Pro Leu Glu Pro His Pro Pro Gly Glu Gly Pro Ser
        355                 360                 365

Glu Trp Ser Ser Asp Thr Ala Glu Gly Arg Pro Cys Pro Tyr Pro His
    370                 375                 380

Cys Gln Val Leu Ser Ala Gln Pro Gly Ser Glu Glu Leu Glu Glu
385                 390                 395                 400

Leu Cys Glu Gln Ala Val
                405

<210> SEQ ID NO 39
<211> LENGTH: 284
<212> TYPE: PRT
<213> ORGANISM: Homo sapiens

<400> SEQUENCE: 39

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
                20                  25                  30

Trp Tyr Lys Gly Glu Arg Val Asp Gly Asn Arg Gln Ile Ile Gly Tyr
            35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
    115                 120                 125

Val Ala Phe Thr Cys Glu Pro Glu Thr Gln Asp Ala Thr Tyr Leu Trp
130                 135                 140
```

```
Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
            165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Thr Pro Ile Ile
            195                 200                 205

Ser Pro Asp Ser Ser Tyr Leu Ser Gly Ala Asn Leu Asn Leu Ser
    210                 215                 220

Cys His Ser Ala Ser Asn Pro Ser Pro Gln Tyr Ser Trp Phe Val Asn
225                 230                 235                 240

Gly Thr Phe Gln Gln His Thr Gln Val Leu Leu Ile Ala Lys Ile Gln
                245                 250                 255

Pro Asn Asn Asn Gly Thr Tyr Ala Cys Phe Val Ser Asn Leu Ala Thr
                260                 265                 270

Gly Arg Asn Asn Ser Ile Val Lys Ser Ile Thr Val
                275                 280

<210> SEQ ID NO 40
<211> LENGTH: 407
<212> TYPE: PRT
<213> ORGANISM: Pseudomonas aeruginosa

<400> SEQUENCE: 40

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu
        50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
                100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
        130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
            195                 200                 205

Leu Ala Gln Gln Arg Cys Asn Leu Asp Asp Thr Trp Glu Gly Lys Ile
        210                 215                 220

Tyr Arg Val Leu Ala Gly Asn Pro Ala Lys His Asp Leu Asp Ile Lys
225                 230                 235                 240
```

```
Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val
                405

<210> SEQ ID NO 41
<211> LENGTH: 61
<212> TYPE: PRT
<213> ORGANISM: Pseudomonas aeruginosa

<400> SEQUENCE: 41

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg
    50                  55                  60

<210> SEQ ID NO 42
<211> LENGTH: 313
<212> TYPE: PRT
<213> ORGANISM: Pseudomonas aeruginosa

<400> SEQUENCE: 42

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95
```

```
Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
            130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
            195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
            275                 280                 285

Tyr Pro Val Gln Arg Leu Val Ala Leu Tyr Leu Ala Ala Arg Leu Ser
            290                 295                 300

Trp Asn Gln Val Asp Gln Val Ile Arg
305                 310

<210> SEQ ID NO 43
<211> LENGTH: 15
<212> TYPE: PRT
<213> ORGANISM: Artificial Sequence
<220> FEATURE:
<223> OTHER INFORMATION: NESK

<400> SEQUENCE: 43

Leu Gln Lys Lys Leu Glu Glu Leu Glu Leu Ala Lys Asp Glu Leu
1               5                   10                  15

<210> SEQ ID NO 44
<211> LENGTH: 11
<212> TYPE: PRT
<213> ORGANISM: Artificial Sequence
<220> FEATURE:
<223> OTHER INFORMATION: NES consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
```

```
<400> SEQUENCE: 44

Leu Xaa Xaa Lys Leu Xaa Xaa Leu Xaa Leu Xaa
1               5                   10

<210> SEQ ID NO 45
<211> LENGTH: 11
<212> TYPE: PRT
<213> ORGANISM: Artificial Sequence
<220> FEATURE:
<223> OTHER INFORMATION: NES

<400> SEQUENCE: 45

Leu Gln Lys Lys Leu Glu Glu Leu Glu Leu Ala
1               5                   10

<210> SEQ ID NO 46
<211> LENGTH: 192
<212> TYPE: PRT
<213> ORGANISM: Porcine circovirus

<400> SEQUENCE: 46

Asn Gly Ile Phe Asn Thr Arg Leu Ser Arg Thr Phe Gly Tyr Thr Ile
1               5                   10                  15

Lys Arg Thr Thr Val Lys Thr Pro Ser Trp Ala Val Asp Met Met Arg
                20                  25                  30

Phe Asn Ile Asn Asp Phe Leu Pro Pro Gly Gly Gly Ser Asn Pro Arg
            35                  40                  45

Ser Val Pro Phe Glu Tyr Tyr Ser Ile Ser Lys Val Lys Val Glu Phe
        50                  55                  60

Trp Pro Cys Ser Pro Ile Thr Gln Gly Asp Ser Gly Val Gly Ser Ser
65                  70                  75                  80

Ala Val Ile Leu Asp Asp Asn Phe Val Thr Lys Ala Thr Ala Leu Thr
                85                  90                  95

Tyr Asp Pro Tyr Val Asn Tyr Ser Ser Arg His Thr Ile Thr Gln Pro
            100                 105                 110

Phe Ser Tyr His Ser Arg Tyr Phe Thr Pro Lys Pro Val Leu Asp Ser
        115                 120                 125

Thr Ile Asp Tyr Phe Gln Pro Asn Asn Lys Arg Asn Gln Leu Trp Leu
    130                 135                 140

Arg Leu Gln Thr Ala Gly Asn Val Asp His Val Gly Leu Gly Thr Ala
145                 150                 155                 160

Phe Glu Asn Ser Ile Tyr Asp Gln Glu Tyr Asn Ile Arg Val Thr Met
                165                 170                 175

Tyr Val Gln Phe Arg Glu Phe Asn Leu Lys Asp Pro Pro Leu Asn Pro
            180                 185                 190

<210> SEQ ID NO 47
<211> LENGTH: 328
<212> TYPE: PRT
<213> ORGANISM: classical swine fever virus

<400> SEQUENCE: 47

Arg Leu Ser Cys Lys Glu Asp His Arg Tyr Ala Ile Ser Ser Thr Asn
1               5                   10                  15

Glu Ile Gly Pro Leu Gly Ala Glu Gly Leu Thr Thr Thr Trp Lys Glu
                20                  25                  30

Tyr Ser His Gly Leu Gln Leu Asp Asp Gly Thr Val Arg Ala Ile Cys
            35                  40                  45
```

Ile Ala Gly Ser Phe Lys Val Thr Ala Leu Asn Val Ser Arg Arg
 50                  55                  60

Tyr Leu Ala Ser Leu His Lys Arg Ala Leu Pro Thr Ser Val Thr Phe
 65                  70                  75                  80

Glu Leu Leu Phe Asp Gly Thr Ser Pro Ala Ile Glu Glu Met Gly Glu
                 85                  90                  95

Asp Phe Gly Phe Gly Leu Cys Pro Phe Asp Thr Thr Pro Val Val Lys
                100                 105                 110

Gly Lys Tyr Asn Thr Thr Leu Leu Asn Gly Ser Ala Phe Tyr Leu Val
            115                 120                 125

Cys Pro Ile Gly Trp Thr Gly Val Ile Glu Cys Thr Ala Val Ser Pro
130                 135                 140

Thr Thr Leu Arg Thr Glu Val Val Lys Thr Phe Lys Arg Glu Lys Pro
145                 150                 155                 160

Phe Pro His Arg Ala Asp Cys Val Thr Thr Ile Val Glu Lys Glu Asp
                165                 170                 175

Leu Phe His Cys Lys Leu Gly Gly Asn Trp Thr Cys Val Lys Gly Asn
                180                 185                 190

Pro Val Thr Tyr Thr Gly Gly Gln Val Lys Gln Cys Arg Trp Cys Gly
            195                 200                 205

Phe Asp Phe Lys Glu Pro Asp Gly Leu Pro His Tyr Pro Ile Gly Lys
210                 215                 220

Cys Ile Leu Ala Asn Glu Thr Gly Tyr Arg Val Val Asp Ser Thr Asp
225                 230                 235                 240

Cys Asn Arg Asp Gly Val Val Ile Ser Thr Glu Gly Glu His Glu Cys
                245                 250                 255

Leu Ile Gly Asn Thr Thr Val Lys Val His Ala Leu Asp Gly Arg Leu
                260                 265                 270

Ala Pro Met Pro Cys Arg Pro Lys Glu Ile Val Ser Ser Ala Gly Pro
            275                 280                 285

Val Arg Lys Thr Ser Cys Thr Phe Asn Tyr Thr Lys Thr Leu Arg Asn
290                 295                 300

Lys Tyr Tyr Glu Pro Arg Asp Ser Tyr Phe Gln Gln Tyr Met Leu Lys
305                 310                 315                 320

Gly Glu Tyr Gln Tyr Trp Phe Asp
                325

<210> SEQ ID NO 48
<211> LENGTH: 50
<212> TYPE: PRT
<213> ORGANISM: Foot-and-mouth disease virus

<400> SEQUENCE: 48

Ala Thr Val Tyr Asn Gly Ser Ser Lys Tyr Gly Asp Thr Ser Thr Ser
 1                   5                  10                  15

Asn Val Arg Gly Asp Leu Gln Val Leu Ala Gln Lys Ala Glu Arg Thr
                 20                  25                  30

Leu Pro Thr Ser Phe Asn Phe Gly Ala Ile Lys Ala Thr Arg Val Thr
             35                  40                  45

Glu Leu
     50

<210> SEQ ID NO 49
<211> LENGTH: 15
<212> TYPE: PRT

<213> ORGANISM: Foot-and-mouth disease virus

<400> SEQUENCE: 49

Ala Ala Ile Glu Phe Phe Glu Gly Met Val His Asp Ser Ile Lys
1               5                   10                  15

<210> SEQ ID NO 50
<211> LENGTH: 65
<212> TYPE: PRT
<213> ORGANISM: Foot-and-mouth disease virus

<400> SEQUENCE: 50

Ala Thr Val Tyr Asn Gly Ser Ser Lys Tyr Gly Asp Thr Ser Thr Ser
1               5                   10                  15

Asn Val Arg Gly Asp Leu Gln Val Leu Ala Gln Lys Ala Glu Arg Thr
            20                  25                  30

Leu Pro Thr Ser Phe Asn Phe Gly Ala Ile Lys Ala Thr Arg Val Thr
        35                  40                  45

Glu Leu Ala Ala Ile Glu Phe Phe Glu Gly Met Val His Asp Ser Ile
    50                  55                  60

Lys
65

<210> SEQ ID NO 51
<211> LENGTH: 18
<212> TYPE: PRT
<213> ORGANISM: Paramyxovirus

<400> SEQUENCE: 51

Leu Leu Pro Asn Met Pro Lys Asp Lys Glu Gly Cys Ala Lys Ala Pro
1               5                   10                  15

Leu Glu

<210> SEQ ID NO 52
<211> LENGTH: 11
<212> TYPE: PRT
<213> ORGANISM: Paramyxovirus

<400> SEQUENCE: 52

Pro Asp Glu Gln Asp Tyr Gln Ile Arg Met Ala
1               5                   10

<210> SEQ ID NO 53
<211> LENGTH: 29
<212> TYPE: PRT
<213> ORGANISM: Paramyxovirus

<400> SEQUENCE: 53

Leu Leu Pro Asn Met Pro Lys Asp Lys Glu Gly Cys Ala Lys Ala Pro
1               5                   10                  15

Leu Glu Pro Asp Glu Gln Asp Tyr Gln Ile Arg Met Ala
            20                  25

<210> SEQ ID NO 54
<211> LENGTH: 525
<212> TYPE: PRT
<213> ORGANISM: Artificial Sequence
<220> FEATURE:
<223> OTHER INFORMATION: fusion protein PE407-E7-K3

<400> SEQUENCE: 54

Ala Glu Glu Ala Phe Asp Leu Trp Asn Glu Cys Ala Lys Ala Cys Val

-continued

```
1               5                   10                  15
Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
                35                  40                  45

Leu Glu Gly Gly Asn Asp Ala Leu Lys Leu Ala Ile Asp Asn Ala Leu
                50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
                100                 105                 110

Ile Lys Val Phe Ile His Glu Leu Asn Ala Gly Asn Gln Leu Ser His
                115                 120                 125

Met Ser Pro Ile Tyr Thr Ile Glu Met Gly Asp Glu Leu Leu Ala Lys
                130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
                195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
                260                 265                 270

Thr Arg His Arg Gln Pro Arg Gly Trp Glu Gln Leu Glu Gln Cys Gly
                275                 280                 285

Tyr Pro Val Gln Arg Leu Val Ala Leu Tyr Leu Ala Ala Arg Leu Ser
                290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
                340                 345                 350

Gln Gly Thr Gly Asn Asp Glu Ala Gly Ala Asn Ala Asp Val Val
                355                 360                 365

Ser Leu Thr Cys Pro Val Ala Ala Gly Glu Cys Ala Gly Pro Ala Asp
                370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Glu Phe His Met Val Asp Met His Gly
                405                 410                 415

Asp Thr Pro Thr Leu His Glu Tyr Met Leu Asp Leu Gln Pro Glu Thr
                420                 425                 430
```

Thr Asp Leu Tyr Cys Tyr Glu Gln Leu Asn Asp Ser Glu Glu Glu
        435                 440                 445

Asp Glu Ile Asp Gly Pro Ala Gly Gln Ala Glu Pro Asp Arg Ala His
    450                 455                 460

Tyr Asn Ile Val Thr Phe Cys Cys Lys Cys Asp Ser Thr Leu Arg Leu
465                 470                 475                 480

Cys Val Gln Ser Thr His Val Asp Ile Arg Thr Leu Glu Asp Leu Leu
                485                 490                 495

Met Gly Thr Leu Gly Ile Val Cys Pro Ile Cys Ser Gln Lys Pro Leu
        500                 505                 510

Glu Lys Asp Glu Leu Lys Asp Glu Leu Lys Asp Glu Leu
        515                 520                 525

<210> SEQ ID NO 55
<211> LENGTH: 290
<212> TYPE: PRT
<213> ORGANISM: Artificial Sequence
<220> FEATURE:
<223> OTHER INFORMATION: fusion protein RAP1-CD28convPEt-E7-K3

<400> SEQUENCE: 55

Ala Glu Phe Glu Glu Pro Arg Val Ile Asp Leu Trp Asp Leu Ala Gln
1               5                   10                  15

Ser Ala Asn Leu Thr Asp Lys Glu Leu Glu Ala Phe Arg Glu Glu Leu
            20                  25                  30

Lys His Phe Glu Ala Lys Ile Glu Lys His Asn His Tyr Gln Lys Gln
        35                  40                  45

Leu Glu Ile Ala His Glu Lys Leu Arg His Ala Glu Ser Val Gly Asp
    50                  55                  60

Gly Glu Arg Val Ser Arg Ser Arg Glu Lys His Ala Leu Leu Glu Gly
65                  70                  75                  80

Arg Thr Lys Glu Leu Gly Tyr Thr Val Lys Lys His Leu Gln Asp Leu
                85                  90                  95

Ser Gly Arg Ile Ser Arg Ala Arg Glu Leu Thr Asp Ile Tyr Phe Cys
            100                 105                 110

Lys Ile Glu Phe Met Tyr Pro Pro Pro Tyr Leu Asp Asn Glu Lys Ser
        115                 120                 125

Asn Gly Thr Ile Ile His Arg Ala Arg Tyr Lys Arg Gly Trp Glu Gln
    130                 135                 140

Leu Glu Gln Cys Gly Tyr Pro Val Gln Arg Leu Val Ala Leu Tyr Leu
145                 150                 155                 160

Ala Ala Arg Leu Ser Trp Asn Gln Val Asp Gln Val Ile Arg Gly Ser
                165                 170                 175

Glu Phe Met His Gly Asp Thr Pro Thr Leu His Glu Tyr Met Leu Asp
            180                 185                 190

Leu Gln Pro Glu Thr Thr Asp Leu Tyr Cys Tyr Glu Gln Leu Asn Asp
        195                 200                 205

Ser Ser Glu Glu Glu Asp Glu Ile Asp Gly Pro Ala Gly Gln Ala Glu
    210                 215                 220

Pro Asp Arg Ala His Tyr Asn Ile Val Thr Phe Cys Cys Lys Cys Asp
225                 230                 235                 240

Ser Thr Leu Arg Leu Cys Val Gln Ser Thr His Val Asp Ile Arg Thr
                245                 250                 255

Leu Glu Asp Leu Leu Met Gly Thr Leu Gly Ile Val Cys Pro Ile Cys
            260                 265                 270

```
Ser Gln Lys Pro Leu Glu Lys Asp Glu Leu Lys Asp Glu Leu Lys Asp
        275                 280                 285
Glu Leu
    290
```

VACCINE COMPOSITION COMPRISING AN IMMUNOGENIC PROTEIN AND COMBINATION ADJUVANTS FOR USE IN ELICITING ANTIGEN-SPECIFIC T-CELL RESPONSES

REFERENCE TO RELATED APPLICATION

The present application claims the priority to U.S. Provisional Application Ser. No. 62/121,406, filed Feb. 26, 2015, which is herein incorporated by reference in its entirety.

FIELD OF THE INVENTION

The present invention relates generally to vaccine formulations, and more specifically to vaccine formulations with combination adjuvants.

BACKGROUND OF THE INVENTION

Adjuvants are critical components of many vaccines. The majority of existing vaccines contain a single adjuvant. Owing to their inherent limitations, no single adjuvant is capable of inducing all the protective immune responses required in the many different vaccines. Therefore, there is a need for exploring the potential of using formulations with multiple adjuvants in a vaccine.

SUMMARY OF THE INVENTION

In one aspect, the invention relates to a vaccine composition comprising:
(a) a therapeutically effective amount of an immunogenic protein comprising at least an antigen of a pathogen;
(b) a saponin-base adjuvant selected from the group consisting of GPI-0100, Quil A, QS-21; and
(c) a Toll-like receptor (TLR) agonist adjuvant selected from the group consisting of monophosphoryl lipid A (MPL), and CpG1826.

In another embodiment of the invention, the composition further comprises at least one additive selected from the group consisting of mannitol, sucrose, trehalose, histindine, glycine, arginine, sorbitol, Polysorbate 80, glucose, lactose, maltose, maltodextrins, citrate, Tris and sodium phosphate.

In another embodiment of the invention, the immunogenic protein is a fusion protein comprising:
(a) an antigen-presenting cell (APC)-binding domain or a CD91 receptor-binding domain, located at the N-terminus of the fusion protein;
(b) a protein transduction domain, located at the C-terminus of the APC-binding domain or the CD91 receptor-binding domain, the protein transduction domain being selected from the group consisting of:
  (i) a fusion polypeptide comprising:
    (1) a T cell sensitizing signal-transducing peptide consisting of 28-53 amino acid residues in length, comprising the amino acid sequence of SEQ ID NO: 31, in which $Xaa^8$ is I or L; $Xaa^{10}$ is V, F or A, $Xaa^{11}$ is M or L, $Xaa^{17}$ is L or I, being located at the N-terminus of the fusion polypeptide;
    (2) a translocation peptide consisting of 34-112 amino acid residues in length, comprising an amino acid sequence that is at least 90% identical to SEQ ID NO: 3, 20, 4, or 41; and
    (3) a linker, comprising SEQ ID NO: 15 linking the T cell sensitizing signal-transducing peptide and the translocation peptide;
  (ii) a T cell-sensitizing signal-transducing peptide consisting of 28-53 amino acid residues in length, comprising the amino acid sequence of SEQ ID NO: 31, in which $Xaa^8$ is I or L; $Xaa^{10}$ is V, F or A, $Xaa^{11}$ is M or L, $Xaa^{17}$ is L or I; and
  (iii) a translocation peptide of 34-61 amino acid residues in length, comprising an amino acid sequence that is at least 90% identical to SEQ ID NO: 3, 20, or 41; and
(c) an antigen of a pathogen, located at the C-terminus of the protein transduction domain;
wherein the APC-binding domain or the CD91 receptor-binding domain is free of the amino acid sequence of Pseudomonas exotoxin A (PE) binding domain Ia if the protein transduction domain is the translocation peptide in (biii).

In another embodiment of the invention, the protein transduction domain comprises the sequence of SEQ ID NO: 30.

In another embodiment of the invention, the APC-binding domain or the CD91 receptor-binding domain is a polypeptide comprising an amino acid sequence that is at least 90% identical to the sequence selected from the group consisting of SEQ ID NOs: 5, 9, 6, 7, and 8.

In another embodiment of the invention, the APC-binding domain or the CD91 receptor-binding domain comprises an amino acid sequence that is at least 95% identical to the sequence selected from the group consisting of SEQ ID NOs: 5, 9, 6, 7, and 8.

In another embodiment of the invention, the APC-binding domain or the CD91 receptor-binding domain is a polypeptide comprising an amino acid sequence selected from the group consisting of SEQ ID NOs: 5, 9, 6, 7, and 8.

Alternatively, the APC-binding domain is selected from the group consisting of receptor-associated protein-1 (RAP1) domain III, alpha-2-macroglobulin receptor-associated protein (A2M), HIV-Tat, and heat shock proteins (HSPs), and Pseudomonas exotoxin A (PE) binding domain Ia.

In another embodiment of the invention, the fusion protein is free of the amino acid sequence of Pseudomonas exotoxin A (PE) binding domain Ia.

In another embodiment of the invention, the fusion protein further comprises an endoplasmic reticulum retention sequence located at the C-terminus of the fusion protein.

In another embodiment of the invention, the endoplasmic reticulum (ER) retention sequence comprises the amino acid sequence of Lys-Asp-Glu-Leu (SEQ ID NO: 14). The ER retention sequence may comprise a sequence selected from the group consisting of SEQ ID NOs: 14, 16-19. Alternatively, the ER retention sequence may consist of a sequence selected from the group consisting of SEQ ID NOs: 16-19.

In another embodiment of the invention, the fusion protein is free of an endoplasmic reticulum retention sequence at C-terminus thereof if the antigen contains 10 or more epitopes.

In another embodiment of the invention, the protein transduction domain is the fusion polypeptide in (bi).

In another embodiment of the invention, the protein transduction domain is the T cell-sensitizing signal-transducing peptide in (bii).

In another embodiment of the invention, the fusion protein further comprises an additional linker between the protein transduction domain and the antigen, the additional linker comprising SEQ ID NO: 15.

In another embodiment of the invention, the protein transduction domain is the translocation peptide in (biii).

In another embodiment of the invention, the fusion protein further comprises an additional linker between the APC-binding domain or the CD91 receptor-binding domain and the translocation peptide, the additional linker comprising SEQ ID NO: 15.

In another embodiment of the invention, the protein transduction domain comprises the sequence of SEQ ID NO: 30.

In another embodiment of the invention, the T cell sensitizing signal-transducing peptide comprises an amino acid sequence that is at least 90% identical to SEQ ID NO: 1 or 2.

In another embodiment of the invention, the T cell sensitizing signal-transducing peptide comprises an amino acid sequence selected from the group consisting of SEQ ID NOs: 1 and 2.

In another embodiment of the invention, the translocation peptide comprises an amino acid sequence selected from the group consisting of SEQ ID NO: 3, 20, 4, and 41.

In another embodiment of the invention, the translocation peptide has 34-61 amino acid residues in length.

In another embodiment of the invention, the protein transduction domain of the fusion protein as aforementioned possesses the following features: (i) the T cell-sensitizing signal-transducing peptide comprises the amino acid sequence of SEQ ID NO: 1 or 2; and (ii) the translocation peptide comprises the amino acid sequence that is at least 95% identical to SEQ ID NO: 3.

The T cell sensitizing signal-transducing peptide exhibits a characteristic of eliciting an antibody that recognizes and binds to the amino acid sequence of $K^1X^2E^3X^4X^5Y^6P^7P^8P^9Y^{10}$ (SEQ ID NO: 32) of CD28 receptor on T cells, wherein $X^2$ is I or L; $X^4$ is V, F or A, and $X^5$ is M or L.

The antigen-presenting cell (APC) may be selected from the group consisting of dendritic cells, macrophages, B-cells and monocytes.

In one embodiment of the invention, the cell membrane of the APC comprises a CD91 receptor.

In another embodiment of the invention, the pathogen is at least one selected from the group consisting of Human Papillomavirus (HPV), Porcine Reproductive and Respiratory Syndrome Virus (PRRSV), Human Immuno-deficient Virus (HIV-1), flu virus, dengue virus, Hepatitis C virus (HCV), Hepatitis B virus (HBV) and Porcine Circovirus 2 (PCV2).

In one embodiment of the invention, the antigen of a pathogen is selected from the group consisting of Human Papillomavirus (HPV) E7 protein, Hepatitis B virus (HBV) HBx protein, Hepatitis C virus (HCV) core antigen, Flu virus M2 antigen, and a tumor associated antigen.

In one embodiment of the invention, the HPV E7 protein comprises an amino acid sequence that is at least 90% identical to SEQ ID NO: 21.

In another embodiment of the invention, the tumor associated antigen is selected from the group consisting of SSX2, MAGE-A3, NY-ESO-1, iLRP, WT12-281, RNF43 (2-116+ 696-783), and CEA-NE3.

In another embodiment of the invention, the antigen is HPV E7 antigen comprising an amino acid sequence that is at least 90% identical to the sequence selected from the group consisting of SEQ ID NO: 21 and 22. In a preferred embodiment of the invention, the antigen is HPV E7 antigen comprising an amino acid sequence of SEQ ID NO: 21.

In another embodiment of the invention, the fusion protein further comprises an endoplasmic reticulum retention sequence located at the C-terminus of the fusion protein.

In one embodiment of the invention, the immunogenic protein is a fusion protein comprising the sequence of SEQ ID NO: 54. For example, the immunogenic protein is fusion protein $PE_{407}$-E7-K3 (SEQ ID NO: 54).

In another embodiment of the invention, the immunogenic protein is a fusion protein comprising the sequence of SEQ ID NO: 55. For example, the immunogenic protein is fusion protein RAP1-CD28convPE$_t$-E7-K3 (SEQ ID NO: 55).

In another embodiment of the invention, the immunogenic protein is a fusion protein comprising:
(a) an antigen-presenting cell (APC)-binding domain or a CD91 receptor-binding domain, located at the N-terminus of the fusion protein:
(b) a translocation peptide of 34-112 amino acid residues in length, comprising an amino acid sequence that is at least 90% identical to SEQ ID NO: 3, 4, 20, or 41, located at the C-terminus of the APC-binding domain or the CD91 receptor-binding domain; and
(c) an antigen of a pathogen;
(d) a nuclear export signal, comprising the amino acid sequence of SEQ ID NO: 44; and
(e) an endoplasmic reticulum retention sequence, located at the C-terminus of the fusion protein; wherein the nuclear export signal is located between the antigen and the endoplasmic reticulum retention sequence, or between the translocation peptide and the antigen.

In another embodiment of the invention, the immunogenic protein is a fusion protein comprising:
(a) an antigen-presenting cell (APC)-binding domain or a CD91 receptor-binding domain, located at the N-terminus of the fusion protein:
(b) a translocation peptide of 34-61 amino acid residues in length, comprising an amino acid sequence that is at least 90% identical to SEQ ID NO: 3, 20, or 41, located at the C-terminus of the APC-binding domain or the CD91 receptor-binding domain; and
(c) an antigen of a pathogen;
(d) a nuclear export signal, comprising the amino acid sequence of SEQ ID NO: 44; and
(e) an endoplasmic reticulum retention sequence, located at the C-terminus of the fusion protein; wherein the nuclear export signal is located between the antigen and the endoplasmic reticulum retention sequence, or between the translocation peptide and the antigen.

In another embodiment of the invention, the C-terminal amino acid of the SEQ ID NO: 44 is alanine.

In another embodiment of the invention, the nuclear export signal comprises the amino acid sequence of SEQ ID NO: 45.

In another embodiment of the invention, the endoplasmic reticulum retention sequence comprises the amino acid sequence of SEQ ID NO: 14.

In another embodiment of the invention, the nuclear export signal and the ER retention sequence forms a fusion peptide comprising an amino acid sequence that is at least 90% identical to SEQ ID NO: 43.

In another embodiment of the invention, the translocation peptide has 34-61 amino acid residues in length.

In another embodiment of the invention, the translocation peptide has 34-46 amino acid residues in length.

In another embodiment of the invention, the APC-binding domain or the CD91 receptor-binding domain is free of the amino acid sequence of *Pseudomonas* exotoxin A (PE) binding domain Ia.

In another embodiment of the invention, the APC-binding domain or the CD91 receptor-binding domain comprises the amino acid sequence of SEQ ID NO: 5.

In another embodiment of the invention, the amino acid sequence of the APC-binding domain or the CD91 receptor-binding domain is SEQ ID NO: 9.

In another embodiment of the invention, the antigen is a fusion antigen of two or more antigenic peptides from a pathogen.

In another embodiment of the invention, the ER retention sequence has more than 4 amino acid residues in length.

In another embodiment of the invention, the translocation peptide comprises an amino acid sequence that is at least 95% identical to SEQ ID NO: 3, 4, 20, or 41.

In another embodiment of the invention, the APC-binding domain or the CD91 receptor-binding domain exhibits a characteristics of recognizing and binding to a receptor on an antigen-presenting cell (APC) selected from the group consisting of dendritic cells, monocytes, B-cells and lymphocytes.

In another embodiment of the invention, the pathogen is selected from the group consisting of Porcine reproductive and respiratory syndrome virus (PRRSV), Porcine Circovirus 2 (PCV2), Foot-and-mouth disease virus (FMDV), Classical Swine Fever Virus (CSFV), Newcastle disease virus (NDV), Transmissible gastroenteritis virus (TGEV), Porcine epidemic diarrhea virus (PEDV), Influenza virus, Pseudorabies virus, Parvovirus, Pseudorabies virus, Swine vesicular disease virus (SVDV), Poxvirus, Rotavirus, *Mycoplasma* pneumonia, Herpes virus, Infectious bronchitis, and Infectious bursal disease virus.

The composition may be in a dosage form for parenteral, such as for subcutaneous or intramuscular injection.

In another aspect, the invention relates to use of the composition as aforementioned in the manufacture of a medicament for inducing enhanced antigen-specific T cell-mediated immune responses in a subject in need thereof.

Alternatively, in another aspect, the invention relates to the composition as aforementioned for use in inducing enhanced antigen-specific T cell-mediated immune responses in a subject in need thereof.

Further alternatively, the invention relates to a method of inducing enhanced antigen-specific T cell-mediated immune responses in a subject in need thereof comprising administering the subject in need thereof a therapeutically effective amount of the composition as aforementioned and thereby inducing enhanced antigen-specific T cell-mediated immune responses in a subject in need thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows a schematic drawing of constructs.

FIG. 2 is a table showing cell mediated immunogenicity induced by various vaccine compositions.

FIG. 3 is a table showing humoral immunogenicity induced by various vaccine compositions.

FIG. 4 shows an immunization schedule.

FIG. 5A is a graph showing the interaction of the saponin-base adjuvant GPI-0100 and TLR agonist adjuvant for stimulation of a T cell-mediated immune response elicited by the immunogenic protein $PE_{407}$-E7-K3.

FIG. 5B shows a graph of the data in FIG. 5A normalized to GPI-0100 (50 μg/dose).

FIG. 6 is a graph showing antibody titers from animal groups of FIG. 5A.

FIG. 7A is a graph showing the interaction of the saponin-base adjuvant QS-21 and TLR agonist adjuvant for stimulation of a T cell-mediated immune response elicited by the immunogenic protein $PE_{407}$-E7-K3.

FIG. 7B shows a graph of the data in FIG. 7A normalized to QS-21 (10 μg/dose).

FIG. 7C shows a graph of the data in FIG. 7A normalized to GPI-0100 (100 μg/dose).

FIG. 8 is a graph showing antibody titers from animal groups of FIG. 7A.

FIG. 9 is a graph showing a T cell-mediated immune response elicited by various vaccine formulations as indicated.

FIG. 10A is a table showing various vaccine formulations comprising an immunogenic protein and one or two adjuvants.

FIG. 10B shows an immunization schedule in a tumor mouse model.

FIG. 11 is a graph showing tumor size curves from animal groups vaccinated with $PE_{407}$-E7-K3 in combination with various adjuvants (n=4). The placebo group was treated with PBS (i.e., without adjuvant and $PE_{407}$-E7-K3).

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

Immunogenic proteins such as fusion proteins for use as immunogenic enhancers for inducing antigen-specific T cell responses are disclosed in the U.S. Patent No. 20140154285 A1 and 20140154280 A1, each of which is incorporated herein by reference in its entirety.

A Toll like receptor (TLR) 4 ligand, particularly an agonist such as a lipid A derivative particularly monophosphoryl lipid A or more particularly 3 Deacylated monophoshoryl lipid A (3 D-MPL). 3D-MPL is sold under the name MPL by GlaxoSmithKline Biologicals N.A. and is referred throughout the document as MPL or 3D-MPL.

Quil A (derived from the bark of the South American tree *Quillaja Saponaria* Molina), and fractions thereof are described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1.

QS-21 is a natural saponin derived from the bark of *Quillaja saponaria* Molina. QS-21 is a HPLC purified non-toxic fraction of Quil A and it is disclosed in U.S. Pat. No. 5,057,540.

The term "an antigen-presenting cell (APC) or accessory cell" refers to a cell that displays foreign antigens complexed with major histocompatibility complexes (MHC's) on their surfaces. T-cells may recognize these complexes using their T-cell receptors (TCRs). These cells process antigens and present them to T-cells. Main types of professional antigen-presenting cell: dendritic cells (DCs), macrophages, monocytes, and certain B-cells.

The term "an antigen-presenting cell (APC)-binding domain" refers to a domain that can bind to an antigen-presenting cell (APC). The APC-binding domain may be a polypeptide comprising an amino acid sequence that is at least 90% identical to the sequence selected from the group consisting of SEQ ID NOs: 5, 6, 7, 8, and 9. An APC-binding domain is a ligand that recognizes and binds to a receptor on APC.

Cluster of differentiation 91 (CD91) is a protein that forms a receptor in the membrane of cells and is involved in receptor-mediated endocytosis.

The term "a protein transduction domain" refers to a polypeptide or a fusion polypeptide having a function to sensitize T-cells and thus enhance antigen-specific T cell responses, and/or to guide or direct an antigen toward (i.e., to target to) class I major histocompatibility complex (MHC-1) pathway (i.e., a cytotoxic T cell pathway) of antigen presentation.

The term "to sensitize T cells" generally means that CD8+ and CD4+ T cells are sensitized and as a result, CD8+(CTL) and CD4+ T cell responses to an antigen challenge are enhanced. An antigen-specific cell mediated immune response is measured by quantifying the production of antigen-specific induced γ-interferon in response to an antigen. For example, without a sensitization signal (i.e., without the protein transduction domain), an antigen alone may induce weak or no cell mediated immune response at all, i.e., weak or no production of antigen-specific γ-interferon from CD8+ and CD4+ T cells, while in the presence of a sensitization signal (the protein transduction domain), the antigen may induce an enhanced cell mediated immune response. Thus, the function of a sensitization signal (the protein transduction domain) is to sensitize CD4+ and CD8+ T cells in a host so that when the host is later challenged by an antigen, the antigen can induce an enhanced antigen-specific T cell mediated immune response due to prior CD4+ and CD8+ T cell sensitization.

A protein transduction domain may be "a fusion polypeptide", in which the fusion polypeptide comprises a T cell sensitizing signal-transducing peptide, a linker, and a translocation peptide. For example, the fusion polypeptide may be the polypeptide "CD28convPE$_t$".

The term "CD28conv" refers to a CD28 conserved region, which is a "T cell sensitizing signal-transducing peptide". It's an epitope for inducing CD28 agonist antibody.

The term "PE$_t$" or "PE$_t$Core" refers to a PE translocation domain core with 34 amino acid residues in length.

A linker is present between the "CD28conv" and the "PE$_t$". The orientation or arrangement of the fusion polypeptide "CD28convPE$_t$" is important in that "CD28conv" (or the T cell sensitizing signal-transducing peptide) must be at the upstream to the PE$_t$ (or the translocation peptide), i.e., PE$_t$ must be at the C-terminus of the "CD28conv" to obtain enhanced T-cell responses. The "CD28convPE$_t$" can raise much higher IgG titer (called CD28-specific agonist antibody) specific to CD28conv than the reversed orientation fusion peptide PE$_t$CD28conv. The CD28-specific agonist antibody can sensitize both CD4+ and CD8+ T cells. The correct orientation fusion polypeptide CD28convPE$_t$ contains a linker ($R^1X^2R^3X^4K^5R^6$) between CD28conv and PE$_t$ domains. The linker contains an antigen presenting cell (APC)-specific protease (cathepsin L) cutting site Lys-Arg (KR). Therefore, the fusion protein RAP1-CD28convPE$_t$-Antigen-K3 can be digested into the two fragments: RAP1-CD28conv and PE$_t$-Antigen-K3. The RAP1-CD28conv fragment can be further digested in the lysosome and the epitope of CD28conv is then presented to the APC cell surface via MHC II pathway, which in turn elicits a humoral immune response producing CD28 agonist antibody. Thus, CD28 agonist antibody is produced by B cells. This CD28 agonist antibody can bind to CD28 on the T cell surface and pre-activate the T cells (CD4+ and CD8+ T cells).

A "T cell-sensitizing signal-transducing peptide" has 28-53 amino acid residues in length and comprises an amino acid sequence that is at least 90% identical to SEQ ID NO: 31, in which $X^8$ is I or L; $X^{10}$ is V, F or A. $X^{11}$ is M or L, $X^{17}$ is L or I.

The T cell-sensitizing signal-transducing peptide comprises the critical region $K^1X^2E^3X^4X^5Y^6P^7P^8P^9Y^{10}$ (SEQ ID NO: 32), wherein $X^2$ is I or L; $X^4$ is V, F or A, $X^5$ is M or L.

A T cell sensitizing signal-transducing peptide (TDIYFCKIEFMYPPPYLDNEKSNGTIIH; SEQ ID NO: 31, wherein $X^8$ is L. $X^{10}$ is F, $X^{11}$ is M, $X^{17}$ is L) specific for mice was illustrated in the U.S. Patent No. 20140154285 A1.

A PE translocation peptide may comprise an amino acid sequence that is at least 90% identical to SEQ ID NO: 3, 4, 20 or 41. For example, the amino acid sequence of a PE translocation peptide may be a.a. 280-a.a. 313 (SEQ ID NO: 3), a.a. 268-a.a. 313 (SEQ ID NO: 20), a.a. 253-a.a. 313 (SEQ ID NO: 41), or a.a. 253-a.a. 364 (SEQ ID NO: 4) of full length PE (SEQ ID NO: 10). That is, the amino acid sequence of a PE translocation peptide may contain any region of the PE domain II (a.a. 253 to a.a. 364; SEQ ID NO: 4) as long as it comprises a.a. 280-a.a. 313 (SEQ ID NO: 3) essential fragment.

An antigen may be a pathogenic protein, polypeptide or peptide that is responsible for a disease caused by the pathogen, or is capable of inducing an immunological response in a host infected by the pathogen, or tumor-associated antigen (TAA) which is a polypeptide specifically expressed in tumor cells. The antigen may be selected from a pathogen or cancer cells including, but not limited to, Human Papillomavirus (HPV), Porcine reproductive and respiratory syndrome virus (PRRSV), Human immunodeficiency virus-1 (HIV-1), flu virus, Dengue virus, Hepatitis C virus (HCV), Hepatitis B virus (HBV), Porcine Circovirus 2 (PCV2), Classical Swine Fever Virus (CSFV), Foot-and-mouth disease virus (FMDV), Newcastle disease virus (NDV), Transmissible gastroenteritis virus (TGEV), Porcine epidemic diarrhea virus (PEDV), Influenza virus, Pseudorabies virus, Parvovirus, Pseudorabies virus, Swine vesicular disease virus (SVDV), Poxvirus, Rotavirus, *Mycoplasma pneumonia*. Herpes virus, infectious bronchitis, or infectious bursal disease virus, non-small cell lung cancer, breast carcinoma, melanoma, lymphomas, colon carcinoma, hepatocellular carcinoma and any combination thereof. For example, HPV E7 protein (E7), HCV core protein (HCV core), HBV X protein (HBx) were selected as antigens for vaccine development. The antigen may be a fusion antigen from a fusion of two or more antigens selected from one or more pathogenic proteins. For example, a fusion antigen of PRRSV ORF6 and ORF5 fragments, or a fusion of antigenic proteins from PRRSV and PCV2 pathogens.

The function of an endoplasmic reticulum retention sequence is to assist translocation of an antigen from an endocytotic compartment into ER and retains it in the lumen. It comprises the sequence Lys Asp Glu Leu (KDEL) or RDEL. An ER retention sequence may comprise, or consists essentially of, or consist of, the sequence KKDL-RDELKDEL (SEQ ID NO: 16), KKDELRDELKDEL (SEQ ID NO: 17), KKDELRVELKDEL (SEQ ID NO: 18), or KDELKDELKDEL (SEQ ID NO: 19).

Receptor-associated protein (RAP1) with a molecular weight of 39 kDa is an ER resident protein and molecular chaperone for LDL receptor-related protein. It has a high binding affinity to CD91 (Kd~3 nM) and is composed by three functional-similar domains.

The $PE_{407}$, (SEQ ID NO: 40) is described in prior patent (U.S. Pat. No. 7,335,361 B2) as PE(ΔIII).

A nuclear export signal (NES) refers to a short amino acid sequence of 4 hydrophobic residues in a protein that targets it for export from the cell nucleus to the cytoplasm through the nuclear pore complex using nuclear transport. The NES is recognized and bound by exportins. The most common spacing of the hydrophobic residues to be $L^1X^2X^3K^4L^5X^6X^7L^8X^9L^{10}X^{11}$ (SEQ ID NO. 44), where "L" is leucine, "K" is lysine and "$X^{2,3,6,7,9,11}$" is any naturally occurring amino acid. For example, an artificial NES may comprise the sequence Leu Gln Lys Lys Leu Glu Glu Leu Glu Leu Ala (LQKKLEELELA: SEQ ID NO: 45).

The term "NESK" refers to a fusion peptide of a NES and an ER retention signal (i.e., a NES fused to an ER retention signal). It is an artificial peptide possessing the function of a nuclear export signal (NES) and an ER retention sequence. Thus, it can export an antigen from the cell nucleus to the cytoplasm through the nuclear pore complex, and assist translocation of an antigen from the cytoplasm to ER and retain the antigen in the lumen of the ER. For example, the amino acid sequence of NESK may be LQKKLEELE-LAKDEL (SEQ ID NO: 43).

The term "subject" refers to a human or a non-human animal.

The term "treating" or "treatment" refers to administration of an effective amount of the fusion protein to a subject in need thereof, who has cancer or infection, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

The term "an effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

Abbreviations: CD 28, Cluster of Differentiation 28.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Immunogenic Protein Preparation:

The immunogenic proteins were expressed in *E. coli* expression system. They may be antigen itself only, or antigen and a ER retention signal (K3) fused to the C-terminus of *Pseudomonas* exotoxin A domains I and II (i.e., $PE_{407}$) to generate $PE_{407}$-(antigen)-K3 fusion protein or antigen and a ER retention signal fused to the C-terminus of RAP1-CD28convPE$_t$ fusion protein to generate RAP1-CD28convPE$_t$-(Antigen)-K3 fusion protein (FIG. 1). The antigen used herein was E7 antigen, and the produced two fusion protein $PE_{407}$-E7-K3 (SEQ ID NO: 54) and RAP1-CD28convPE$_t$-E7-K3 (SEQ ID NO: 55) were used in the following experiments.

Immunogenicity Analysis of Different Immunogenic Composition:

The E7 immunogenic proteins. E7 antigen, $PE_{407}$-E7-K3 fusion protein, or RAP1-CD28convPE$_t$-E7-K3 fusion protein were combined with different adjuvant, such as alum, GPI-0100 or QS-21, and their immunogenicity were tested in mice. All immunogenic proteins could elicit medium to strong E7 antigen specific humoral immune response when combined with alum, GPI-0100 or QS-21. For E7 antigen specific cell mediated immune responses, weak to strong responses were elicited when E7 antigen or $PE_{407}$-E7-K3 fusion protein were combined with GPI-0100 or QS-21. On the other hand, RAP1-CD28convPE$_t$-E7-K3 fusion protein could elicit medium to strong cell mediated immune response when combined with alum, GPI-0100 and QS-21. These results revealed that GPI-0100 and QS-21 were better adjuvants to stimulate both humoral and cell mediated immune responses. Furthermore, $PE_{407}$-E7-K3 or RAP1-CD28conv$PE_t$-E7-K3 fusion protein could elicit stronger responses than E7 antigen only when combined with saponin based adjuvant, such as GPI-0100 or QS-21.

Animal Study for T Cell-Mediated Immune Response

Female mice C57BL/6 at 5 weeks old of age were purchased from BioLASCO Taiwan Co., Ltd. 5 mice/cage with a 12 hour day/12 hour night light cycle. Given free access to food and water, the mice were housed for one week and maintained under standard conditions prior to experimentation. The immunogenic protein used for illustration was lyophilized $PE_{407}$-E7-K3 (SEQ ID NO: 54), which was produced by The Vax Genetics Vaccine Co., Ltd., and each vial contained 0.6 mg protein. Adjuvants: GPI-0100 (Hawaii Biotech); MPL (Cat. No. 699800P, Avanti); Poly I:C (Cat. No. tlrl-pic-5, InvivoGen); R837 (Cat. No. tlrl-imqs, InvivoGen); R848 (Cat. No. tlrl-r848, InvivoGen); CpG1826 (Cat. No. tlrl-1826, InvivoGen); and Laboratory grade QS-21 (TheVax).

The immunization schedule is as shown in FIG. 4. Mice were vaccinated once per week for 3 weeks with vaccine formulations as indicated in Table 1 and FIGS. 5A-B, 7A-C. All mice were sacrificed 7 days after the last immunization, and the spleens were harvested. Splenocytes were isolated.

Adjuvant Formulations

To investigate the best immune response for immunogenic composition, adjuvant formulations listed in Table 1 were evaluated.

Intracellular-Cytokine Staining of CD8+ Cells.

Splenocytes ($2*10^7$) were plated in 6-well flat-bottom tissue culture plates and incubated for 2 hours at 37° C., and with and without 1 μg/ml $HPV_{16}$-E7 peptide (amino acids 49-57 of full length PE), and Brefeldin A, and Monensin to increased accumulation of cytokines in the cell enhances the detectability of cytokine-producing cells. After incubation, the cells were transferred to test tube at 300×g for 5 min. The supernatants were discarded, the plates were briefly vortexed, and the cells were stained for surface markers at 0.2 mg/sample of fluorescein isothiocyanate-conjugated anti-mouse CD8 (clone 53-6.7, eBioscience), and anti-mouse CD3 (clone 17A2. BioLegend) for 30 min. The cells were washed with 1 ml of fluorescence-activated cell sorter (FACS) buffer (1% FBS in PBS) and IC Fixation solution (eBioscience) by incubation on ice for 30 min in the dark after resuspension in 1 ml of permeabilization wash buffer (BioLegend). The cells were washed twice in Permwash (BD Pharmingen) and then stained for intracellular IFN-γ with allophycocyanin-conjugated anti-mouse IFN-γ (clone XMG1.2, eBioscience), at 0.2 mg/sample diluted in of permeabilization wash buffer for 30 min on ice in the dark. The cells were resuspension in 1 ml FACS buffer and then analyzed on a FACS Calibur flow cytometer.

Figure 5B:
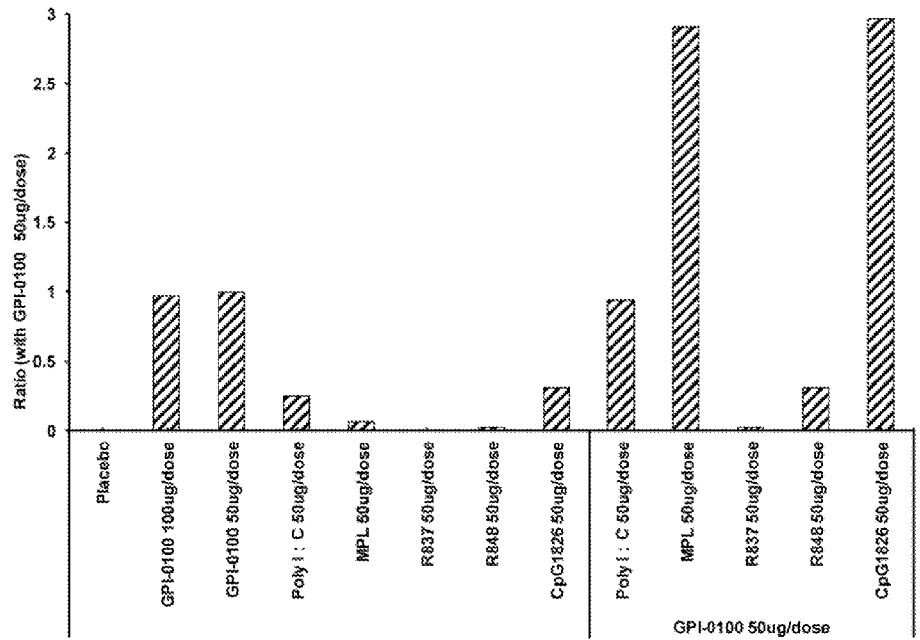

In the immunogenicity assays, antigen-specific T cell-mediated immune responses induced by various vaccine formulations were evaluated by measuring the numbers of CD3+/CD8+/IFNγ+ T cells in the splenocytes. FIG. 5A shows percentage of E7-specific CD8+/IFNγ+ double positive in CD3+ T cells per $2*10^7$ splenocytes from animal groups treated with various vaccine formulations. The data from each group were compared against that of the animal group treated with the combination of $PE_{407}$-K3 and 50 μg/dose of GPI-0100 (FIG. 5B). The data indicated that GPI-0100 in combination with MPL or CpG1826 could

TABLE 1

| Formulation No. | Group I (Saponin-base adjuvants) | | Group II (TLR agonist adjuvants) | | | | | |
|---|---|---|---|---|---|---|---|---|
| | | | | | Imidazolquinoline | | | |
| | QS-21 | GPI-0100 | Poly I:C (TLR3 agonist) | MPL (TLR4 agonist) | R837 (TLR7 agonist) | R848 (TLR7/8 agonist) | CpG1826 (TLR9 agonist) |
| A | | | | Placebo | | | |
| B | | 100 μg | | | | | |
| C | | 50 μg | | | | | |
| D | | | 50 μg | | | | |
| E | | | | 50 μg | | | |
| F | | | | | 50 μg | | |
| G | | | | | | 50 μg | |
| H | | | | | | | 50 μg |
| I | | 50 μg | 50 μg | | | | |
| J | | 50 μg | | 50 μg | | | |
| K | | 50 μg | | | 50 μg | | |
| L | | 50 μg | | | | 50 μg | |
| M | | 50 μg | | | | | 50 μg |
| N | 10 μg | | | | | | |
| O | | | | 10 μg | | | |
| P | | | | | 10 μg | | |
| Q | | | | | | 10 μg | |
| R | | | | | | | 10 μg |
| S | | | | | | | 10 μg |
| T | 10 μg | | 10 μg | | | | |
| U | 10 μg | | | 10 μg | | | |
| V | 10 μg | | | | 10 μg | | |
| W | 10 μg | | | | | 10 μg | |
| X | 10 μg | | | | | | 10 μg | potentiate a T cell-mediated immune response elicited by an immunogenic protein for 2-3 folds.

Figure 7B:
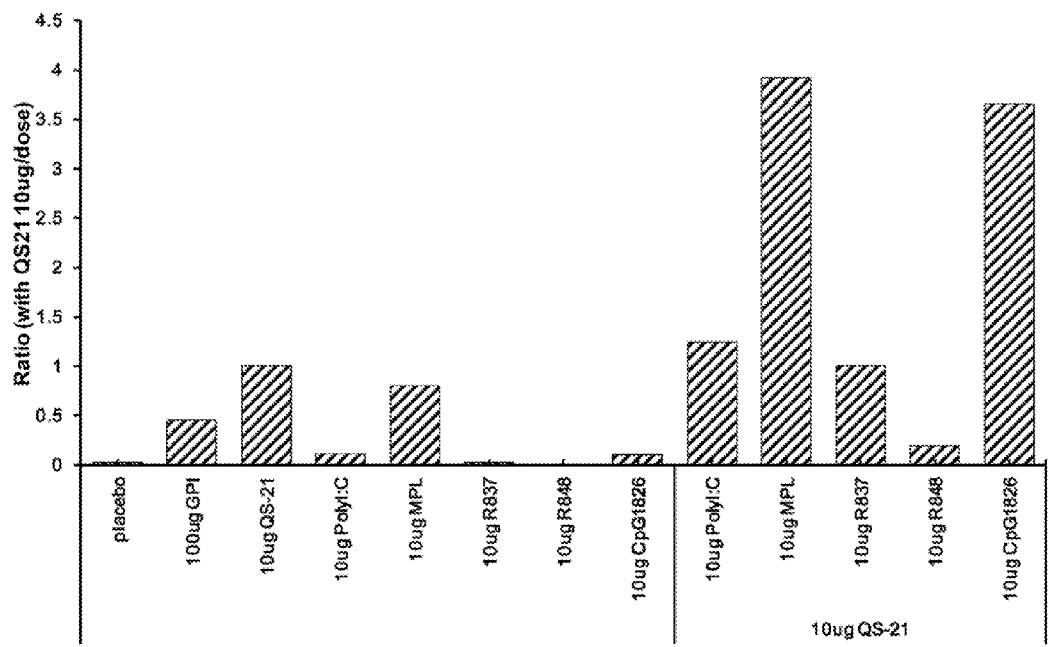
Figure 7C:
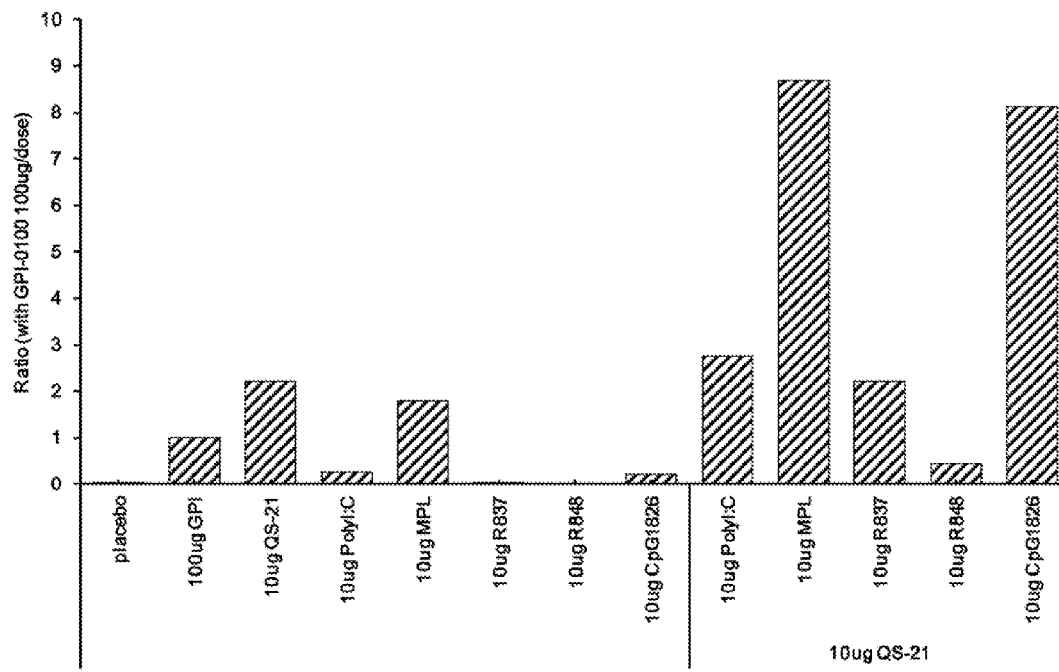

FIG. 7A shows percentage of E7-specific CD8+/IFNγ+ double positive in CD3+ T cells per $2*10^7$ splenocytes from animal groups treated with various vaccine formulations. The data from each group were compared against that of the animal group treated with the combination of $PE_{407}$-E7-K3 and QS-21 (10 μg/dose; FIG. 7B) or GPI-0100 (100 μg/dose; FIG. 7C). The data indicated that QS-21 in combination with MPL (10 μg/dose) or CpG1826 (10 μg/dose) could potentiate the T cell-mediated immune response elicited by the immunogenic protein $PE_{40}$-E7-K3 for 3-4 times as compared to the vaccine composition comprising a single adjuvant, QS-21 (10 μg/dose) alone (FIG. 7B). In addition, the T cell-mediated immune response elicited by the vaccine formulation comprising combination adjuvants, QS-21 and MPL, or QS-21 and CpG1826, was 8 times of the animal group treated with the vaccine formulation comprising a single adjuvant. GPI-0100 (100 μg/dose) alone (FIG. 7C).

Humoral Immunity Studies

Animals were vaccinated and the serum samples were collected as described above. The serum samples from each animal and at each collection time point were diluted for 10000 times in blocking buffer. The level of HPV16 E7 specific IgG was detected by ELISA method (coating E7 pet32a 1 μg/well).

Figure 6:
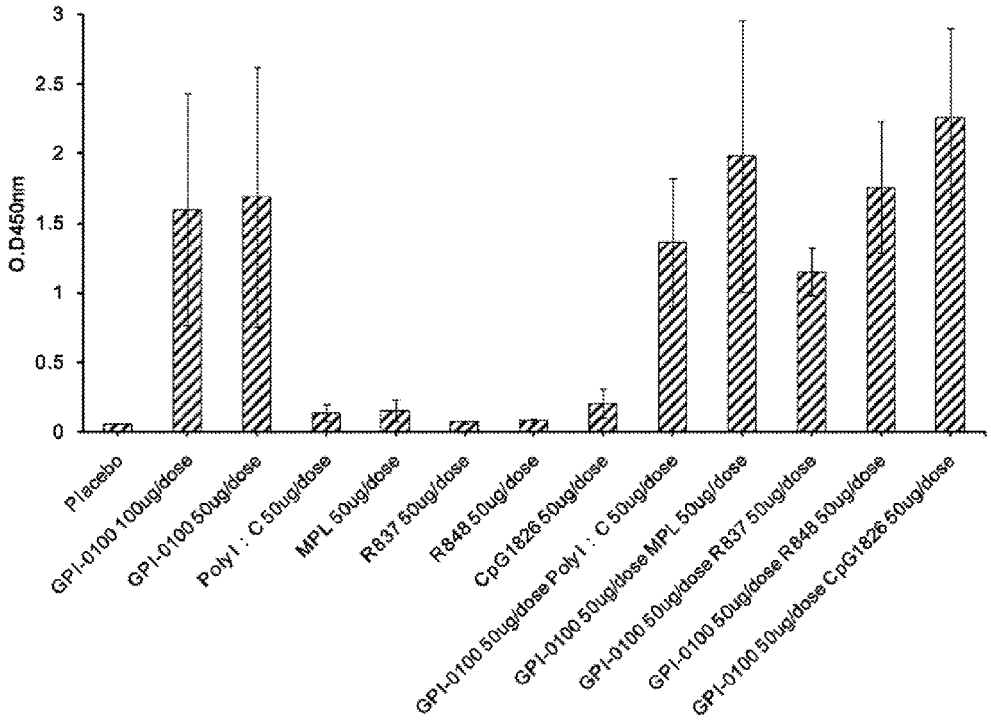

FIG. 6 shows that when a single TLR agonist adjuvant was used in the vaccine composition, only a small amount of antibody was induced, but when the TLR agonist adjuvant was used together with the saponin-base adjuvant GPI-0100 (50 μg/dose), a large amount of antibodies were elicited in the mouse after the 3rd immunization.

Figure 8:
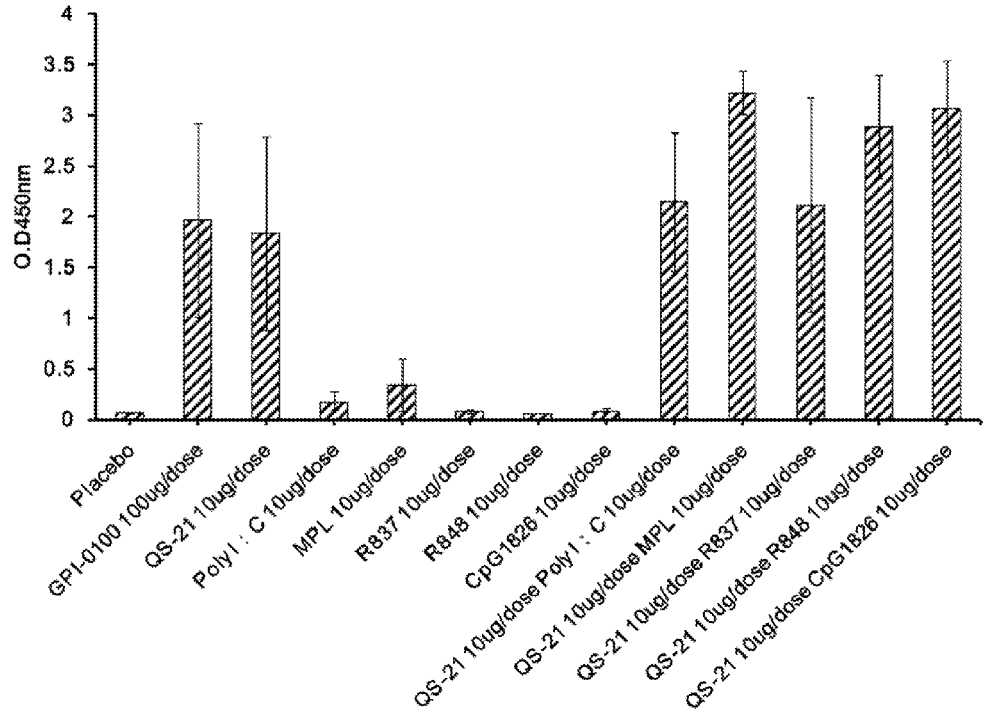

FIG. 8 shows that when a single TLR agonist adjuvant was used in the vaccine composition, only a small amount of antibody was induced, but when the TLR agonist adjuvant was used together with the saponin-base adjuvant QS-21 (10 μg/dose), the animal groups treated with formulations comprising the two adjuvants QS-21+MPL or QS-21+CpG826 produced a large amount of antibodies after the second immunization (Data not shown). QS-21 in combination with all TLR agonist adjuvants produced a large amount of antibodies after the third immunization. The data shows that combination of QS-21 or GPI-0100 and Poly IC does not potentiate the effect of QS-21 or GPI-0100. This suggests that GPI-100 or QS-21 might operate via a TLR3-related mechanism. Imidazolquline adjuvant (R837, R848) works through the same pathway as CpG1826 but exhibits entirely different T cell-mediated immunity. It remains to be investigated whether midazolquline acts through K cells and/or macrophages cells.

T Cell-Mediated Immunogenic Response Elicited by Fusion Proteins of Different Platforms We further examines T cell-mediated immunogenic response elicited by different immunogenic proteins $PE_{407}$-E7-K3 and RAP1-CD28convPE$_t$-E7-K3 using the best combination of adjuvants discovered as described above, and performed the same immunogenicity assays as described in FIG. 5A. Mice 57BL/6 of 5 weeks old age were purchased from BioLASCO Taiwan Co., Ltd. The immunization schedule is as the same as in FIG. 4. Table 2 shows the vaccine formulations used in the studies.

FIG. 9 shows that the fusion protein RAP1-CD28convPE$_t$-E7-K3 elicited a stronger T cell-mediated immune response than the fusion protein $PE_{407}$-E7-K3. However, no matter what type of combination of adjuvants was used, the two platform elicited a similar pattern of the T cell-mediated immune response.

TABLE 2

| Formulation No. | Protein | QS-21 | GPI-0100 | MPL | CpG1826 |
|---|---|---|---|---|---|
| A | | Placebo | | | |
| B | $PE_{407}$-E7-K3 | 10 μg | 50 μg | | |
| C | | | 50 μg | | |
| D | | | 50 μg | 50 μg | |
| E | | | 50 μg | | 50 μg |
| F | | 10 μg | | | |
| G | | 10 μg | | 10 μg | |
| H | | 10 μg | | | 10 μg |
| I | RAP1- | 10 μg | 50 μg | | |
| J | CD28convPE$_t$- | | 50 μg | | |
| K | E7-K3 | | 50 μg | 50 μg | |
| L | | | 50 μg | | 50 μg |
| M | | 10 μg | | | |
| N | | 10 μg | | 10 μg | |
| O | | 10 μg | | | 10 μg |

Studies on TC-1 Tumor Animal Model

Vaccine: 100 μg of $PE_{407}$-E7-K3 is formulated with different adjuvants or combination thereof. Vaccine formulations were shown in FIG. 10A. Seven days after being challenged with TC-1 cell lines ($5*10^4$ cell/mouse, s.c.), mice were immunized every 7 days for a total of three times (FIG. 10B). The results indicate that as compared with the single adjuvant GPI-0100 (100 μg/dose) alone, the combination adjuvants QS-21 (10 μg/dose) and MPL (10 μg/dose), QS-21 (10 μg/dose) and CpG1826 (10 μg/dose), GPI-0100 (50 μg/dose) and MPL (50 μg/dose), or GP-0100 (50 μg/dose) and CpG1826 (50 μg/dose) can effectively inhibit the growth of TC-1 tumor cells (FIG. 11).

Table 3 shows SEQ ID NOs. of the components of various fusion proteins.

Table 4 shows the fusion proteins tested for the effects on T cell-mediated immune responses in animals and the sequences of antigens.

TABLE 3

| Component | SEQ ID NO: | Length (residues) |
|---|---|---|
| hCD28 Core<br>TDIYFCKIEVMYPPPYLDNEKSNGTIIH | 1 | 28 |
| hCD28 Maximum<br>NCDGKLGNESVTFYLQNLYVNQTDIYFCKIEVMYPPPYLDNE<br>KSNGTIIHVKG | 2 | 53 |
| PE$_t$ Core (PE translocation domain core; a.a. 280- a.a. 313 of PE) | 3 | 34 |
| PE$_t$ Maximum (translocation domain maxi, a.a. 253 - a.a. 364 of PE) | 4 | 112 |

TABLE 3-continued

| Component | SEQ ID NO: | Length (residues) |
|---|---|---|
| RAP1 Minimum (domain III of RAP1) | 5 | 104 |
| A2M Minimum | 6 | 153 |
| HIV-Tat Minimum | 7 | 24 |
| HSPs Minimum,. Heat shock 70 kDa protein (HSPs; *Homo sapiens*) | 8 | 641 |
| Minimum *Pseudomonas* exotoxin A (PE) binding domain 1a (an APC-binding domain, a.a. 1- a.a. 252 of PE) | 9 | 252 |
| Linker $R^1X^2R^3X^4K^5R^6$, in which "$X^{2,4}$" is any amino acid residue. | 15 | 6 |
| Full length PE (Exotoxin A mature lbrm, *Pseudomonas aeruginosa*) | 10 | 613 |
| Full length RAP1 (*Homo sapiens* low density lipoprotein receptor-related protein associated protein 1, LRPAP1): Domain 1: a.a. 1-a.a. 112; domain 2: a.a. 113-a.a, 218; domain 3: a.a. 219-aa. 323. | 11 | 323 |
| Full length A2M (*Homo sapiens* alpha-2-macroglobulin receptor associated protein precursor) | 12 | 357 |
| HIV-Tat (Human immunodeficiency virus 1) | 13 | 101 |
| KDEL (endoplasmic reticulum retention sequence) | 14 | 4 |
| KKDLRDELKDEL (K3) | 16 | 12 |
| KKDEIRDELKDEL (K3) | 17 | 13 |
| KKDELRVELKDEL (K3) | 18 | 13 |
| KDELKDELKDEL (K3) | 19 | 12 |
| PE$_{268-313}$(a.a. 268-a.a. 313 of full length PE) PLETFTRHRQPRGWEQLEQCGYPVQRLVALYLAARLSWNQV DQV1R | 20 | 46 |
| CD28comvPEt $T^1D^2I^3Y^4F^5C^6K^7X^8E^9X^{10}X^{11}Y^{12}P^{13}P^{14}P^{15}Y^{16}X^{17}D^{18}N^{19}E^{20}K^{21}S^{22}N^{23}G^{24}T^{25}I^{26}I^{27}H^{28}R^{29}X^{30}R^{31}X^{32}R^{33}R^{34}G^{35}W^{36}E^{37}Q^{38}L^{39}E^{40}Q^{41}C^{42}G^{43}Y^{44}P^{45}V^{46}Q^{47}R^{48}L^{49}V^{50}A^{51}L^{52}Y^{53}L^{54}A^{55}R^{56}R^{57}L^{58}S^{59}W^{60}N^{61}Q^{62}V^{63}D^{64}Q^{65}V^{66}I^{67}R^{68}$, wherein $X^8$ is I or L; $X^{10}$ is V, F or A, $X^{11}$ is M or L, $X^{17}$ is L or I, $X^{30,32}$ is any amino acid residue. | 30 | 68 |
| CD28 consensus sequence $T^1D^2I^3Y^4F^5C^6K^7X^8E^9X^{10}X^{11}Y^{12}P^{13}P^{14}P^{15}Y^{16}X^{17}D^{18}N^{19}E^{20}K^{21}S^{22}N^{23}G^{24}T^{25}I^{26}I^{27}H^{28}$, wherein $X^8$ is I or L; $X^{10}$ is V, F | 31 | 28 |
| CD28 critical region $K^1X^2E^3X^4X^5Y^6P^7P^8P^9Y^{10}$, wherein $X^2$ is I or L; $X^4$ is V, R or A, $X^5$ is M or L. | 32 | 10 |
| SSX2 | 33 | 187 |
| MAGE-A3 | 34 | 314 |
| NY-ESO-1 | 35 | 181 |
| iLRP | 36 | 296 |
| WT12-281 | 37 | 279 |
| RNF43(2-116 + 696-783) | 38 | 406 |
| CEA-NE3 | 39 | 284 |
| PE$_{407}$(a.a. 1-a.a. 407 of full length PE) | 40 | 407 |
| PE$_{253-313}$(a.a. 253-a.a. 313 of full length PE) | 41 | 61 |
| PE$_{313}$(a,a. 1- a.a. 313 of full length PE) | 42 | 313 |
| NESK is LQKKLEELELAKDEL * | 43 | 15 |

TABLE 3-continued

| Component | SEQ ID NO: | Length (residues) |
|---|---|---|
| NES consensus sequence is $L^1X^2X^3K^4L^5X^6X^7L^8X^9L^{10}X^{11}$, wherein "L" is leucine, "K" is lysine and "$X^{2,3,6,7,9,11}$" is any naturally occurring amino acid, | 44 | 11 |
| NES is LQKKLEELELA | 45 | 11 |
| PCV2 ORF2 (Porcine Circovirus type 2 Open Reading Frame 2) | 46 | 192 |
| CSFV E2 (Classical Swine Fever Virus Envelope glycoprotein E2) | 47 | 328 |
| FMDV VP1 peptide (viral capsid protein a.a. 127-a.a. 176 of VP1) | 48 | 50 |
| FMDV 3A peptide (a.a. 21-35 of 3A) | 49 | 15 |
| FMDV (Foot-and-Mouth Disease Virus) VP1-3A peptide** | 50 | 65 |
| NDV F peptide (a.a. 65- a.a. 82 of Fusion protein) | 51 | 18 |
| NDV HN peptide (a.a. 101- a.a. 111 of Hemagglutinin-Neuraminidase) | 52 | 11 |
| NDV FHN peptide *** | 53 | 29 |
| $PE_{407}$-E7-K3 | 54 | 525 |
| RAP1-CD2SconvPE$_t$-E7-K3 | 55 | 290 |

*: The bold letters represents the amino acid sequence of an artificial nuclear exporting signal; the underlined letters represents the amino acid sequence of an endoplasmic reticulum retention signal.
**: The VP1-3A peptide (SEQ ID NO: 50) is a fusion antigen composed of a.a. 127 - a.a. 176 of VP1 and a.a. 21-a.a. 35 of 3A; i.e., a fusion protein of FMDV VP1 peptide (SEQ ID NO: 48) and FMDV 3A peptide (SEQ ID NO 49).
***: The FHN peptide (SEQ ID NO: 53) is a fusion antigen composed of a.a. 65 - a.a. 82 of fusion protein and (a.a. 101-a.a. 111 at Hemaglutinin-Neuranninidase; i.e., a fusion protein of NDV F peptide (SEQ ID NO: 51) and NDV HN peptide (SEQ ID NO: 52).

TABLE 4

| Fusion protein name | Antigen Name | Antigen SEQ ID NO: |
|---|---|---|
| RAP1-CD28convPE$_t$-E7-K3 | HPV16 E7 (full length) | 21 |
| $PE_{407}$-E7-K3 | | |
| RAP1-CD28convPE$_t$-E7$_{18}$-K3 | HPV18 E7 (full length) | 22 |
| RAP1-CD28convPE$_t$-HCVc-K3 | HCV core protein (full length) | 23 |
| RAP1-CD28convPE$_t$-HBx-K3 | HBV X protein (full length) | 24 |
| RAP1-CD28convPE$_t$-PCV2-K3 | PCV2 ORF2 (a fragment of ORF2) | 25 |
| RAP1-CD28convPE$_t$-DGD-K3 | PRRSV nucleocapsid (a fusion antigen: ORF7 a.a. 64-a.a. 123, linker and ORF7 a.a. 64-a.a. 123) | 26 |
| RAP1-CD28convPE$_t$-M12-K3 | PRRSV RNA-dependent RNA polymerase (ORF1b a.a. 1046-a.a. 1210) | 27 |
| RAP1-CD28convPE$_t$-PQAB-K3 | PRRSV American strain: a fusion antigen of ORF6 (a.a. 2-a.a. 26) and ORF5 (a.a. 31-a.a. 63) | 28 |
| RAP1-CD28convPE$_t$-RSAB-K3 | PRRSV European strain: a fusion antigen of ORF6 (a.a. 2-a.a. 28) and ORF5 (a.a. 31-a.a. 64) | 29 |

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. All references cited and discussed in this specification are incorporated herein by reference in their entireties and to the same extent as if each reference was individually incorporated by reference.

What is claimed is:

1. A composition consisting of:
   (a) a therapeutically effective amount of an immunogenic protein;
   (b) the saponin-based adjuvant QS21;
   (c) a Toll-like receptor (TLR) agonist adjuvant selected from the group consisting of monophosphoryl lipid A (MPL), and CpG oligonucleotide; and
   (d) optionally at least one additive selected from the group consisting of mannitol, sucrose, trehalose, histindine, glycine, arginine, sorbitol, Polysorbate 80, glucose, lactose, maltose, maltodextrins, citrate, Tris and sodium phosphate;
   wherein the immunogenic protein is a fusion protein comprising:
   (a') an antigen-presenting cell (APC)-binding domain or a CD91 receptor-binding domain, located at the N-terminus of the fusion protein;
   (b') a protein transduction domain, located at the C-terminus of the APC-binding domain or the CD91 receptor-binding domain, the protein transduction domain being selected from the group consisting of:
      (i) a fusion polypeptide comprising:
         (1) a T cell sensitizing signal-transducing peptide consisting of 28-53 amino acid residues in length, comprising the amino acid sequence of SEQ ID NO: 31, in which $Xaa^8$ is I or L; $Xaa^{10}$ is V, F or A, $Xaa^{11}$ is M or L, $Xaa^{17}$ is L or I, being located at the N-terminus of the fusion polypeptide;
         (2) a translocation peptide consisting of 34-112 amino acid residues in length, comprising an amino acid sequence that is at least 90% identical to SEQ ID NO: 3, 4, 20, or 41; and
         (3) a linker, comprising SEQ ID NO: 15 linking the T cell sensitizing signal-transducing peptide and the translocation peptide;
      (ii) a T cell-sensitizing signal-transducing peptide consisting of 28-53 amino acid residues in length, comprising the amino acid sequence of SEQ ID NO: 31, in which $Xaa^8$ is I or L; $Xaa^{10}$ is V, F or A, $Xaa^{11}$ is M or L, $Xaa^{17}$ is L or I; and
      (iii) a translocation peptide of 34-112 amino acid residues in length, comprising an amino acid sequence that is at least 90% identical to SEQ ID NO: 3, 4, 20 or 41; and
   (c') an antigen of a pathogen, located at the C-terminus of the protein transduction domain.

2. A composition comprising:
   (A) a therapeutically effective amount of an immunogenic protein comprising at least an antigen of a pathogen:
   (B) the saponin-base adjuvant GPI-0100; and
   (C) a Toll-like receptor (TLR) agonist adjuvant selected from the group consisting of monophosphoryl lipid A (MPL), and CpG oligonucleotide, wherein the immunogenic protein is a fusion protein comprising:
   (a) an antigen-presenting cell (APC)-binding domain or a CD91 receptor-binding domain, located at the N-terminus of the fusion protein;
   (b) a protein transduction domain, located at the C-terminus of the APC-binding domain or the CD91 receptor-binding domain, the protein transduction domain being selected from the group consisting of:
      (i) a fusion polypeptide comprising:
         (1) a T cell sensitizing signal-transducing peptide consisting of 28-53 amino acid residues in length, comprising the amino acid sequence of SEQ ID NO: 31, in which $Xaa^8$ is I or L; $Xaa^{10}$ is V, F or A, $Xaa^{11}$ is M or L, $Xaa^{17}$ is L or I, being located at the N-terminus of the fusion polypeptide;
         (2) a translocation peptide consisting of 34-112 amino acid residues in length, comprising an amino acid sequence that is at least 90% identical to SEQ ID NO: 3, 4, 20 or 41; and
         (3) a linker, comprising SEQ ID NO: 15 linking the T cell sensitizing signal-transducing peptide and the translocation peptide;
      (ii) a T cell-sensitizing signal-transducing peptide consisting of 28-53 amino acid residues in length, comprising the amino acid sequence of SEQ ID NO: 31, in which $Xaa^8$ is I or L; $Xaa^{10}$ is V, F or A, $Xaa^{11}$ is M or L, $Xaa^{17}$ is L or I; and
      (iii) a translocation peptide of 34-112 amino acid residues in length, comprising an amino acid sequence that is at least 90% identical to SEQ ID NO: 3, 4, 20, or 41; and
   (c) an antigen of a pathogen, located at the C-terminus of the protein transduction domain.

3. The composition of claim 2, wherein the protein transduction domain comprises the sequence of SEQ ID NO: 30.

4. The composition of claim 2, wherein the APC-binding domain or the CD91 receptor-binding domain is a polypeptide comprising an amino acid sequence that is at least 90% identical to the sequence selected from the group consisting of SEQ II) NOs: 5, 9, 6, 7, and 8.

5. The composition of claim 2, wherein the T cell sensitizing signal-transducing peptide comprises an amino acid sequence selected from the group consisting of SEQ ID NOs: 1 and 2.

6. The composition of claim 2, wherein the translocation peptide comprises the amino acid sequence of SEQ ID NO: 3.

7. The composition of claim 2, wherein the pathogen is at least one selected from the group consisting of Human Papillomavirus (HPV), Porcine Reproductive and Respiratory Syndrome Virus (PRRSV), Human Immuno-deficient Virus (HIV-1), flu virus, dengue virus, Hepatitis C virus (HCV), Hepatitis B virus (HBV) and Porcine Circovirus 2 (PCV2).

8. The composition of claim 2, wherein the antigen of a pathogen is selected from the group consisting of Human Papillomavirus (HPV) E7 protein, Hepatitis B virus (HBV) HBx protein, Hepatitis C virus (HCV) core antigen, Flu virus M2 antigen, and a tumor associated antigen.

9. The composition of claim 8, wherein the tumor associated antigen is selected from the group consisting of SSX2, MAGE-A3, NY-ESO-1, iLRP, WT12-281, RNF43 (2-116+ 696-783), and CEA-NE3.

10. The composition of claim 2, wherein the fusion protein further comprises an endoplasmic reticulum retention sequence located at the C-terminus of the fusion protein.

11. The composition of claim 2, wherein the protein translocation domain is the translocation peptide of 34-112 amino acid residues in length, comprising an amino acid sequence that is at least 90% identical to SEQ ID NO: 3, 4, 20, or 41, located at the C-terminus of the APC-binding domain or the CD91 receptor-binding domain; and the fusion protein further comprises
a nuclear export signal, comprising the amino acid sequence of SEQ ID NO: 44; and
an endoplasmic reticulum retention sequence, located at the C-terminus of the fusion protein; wherein the nuclear export signal is located between the antigen and the endoplasmic reticulum retention sequence, or between the translocation peptide and the antigen.

12. The composition of claim 11, wherein the translocation peptide is of 34-61 amino acid residues in length, comprising an amino acid sequence that is at least 90% identical to SEQ ID NO: 3, 20, or 41.

13. The composition of claim 2, wherein:
(a) the APC-binding domain or the CD91 receptor-binding domain is a polypeptide comprising an amino acid sequence that is at least 90% identical to SEQ ID NO: 9;
(b) the protein transduction domain is the translocation peptide consisting of 34-112 amino acid residues in length, comprising an amino acid sequence that is at least 900/identical to SEQ ID NO: 3, 4, 20 or 41; and
(c) the antigen of a pathogen comprises an amino acid sequence that is at least 90% identical to SEQ ID NO: 21.

14. The composition of claim 13, wherein the fusion protein comprises the amino acid sequence of SEQ ID NO: 54.

15. The composition of claim 2, wherein:
(a) the APC-binding domain or the CD91 receptor-binding domain is a polypeptide comprising an amino acid sequence that is at least 90% identical to SEQ ID NO: 5;
(b) the protein transduction domain comprises the sequence of SEQ ID NO: 30; and
(c) the antigen of a pathogen comprises an amino acid sequence that is at least 90% identical to SEQ ID NO: 21.

16. The composition of claim 15, wherein the fusion protein comprises the amino acid sequence of SEQ ID NO: 55.

17. A method for inducing an enhanced pathogen antigen-specific T cell response, comprising:
administering the composition of claim 2 to a subject in need thereof, and thereby inducing the enhanced pathogen antigen-specific T cell response.

18. A composition consisting of:
(a) a therapeutically effective amount of an immunogenic protein;
(b) the saponin-based adjuvant QS21;
(c) a Toll-like receptor (TLR) agonist adjuvant selected from the group consisting of monophosphoryl lipid A (MPL), and CpG oligonucleotide; and
(d) optionally at least one additive selected from the group consisting of mannitol, sucrose, trehalose, histindine, glycine, arginine, sorbitol, Polysorbate 80, glucose, lactose, maltose, maltodextrins, citrate, Tris and sodium phosphate;
wherein the immunogenic protein is a fusion protein comprising:
(a') an antigen-presenting cell (APC)-binding domain or a CD91 receptor-binding domain, located at the N-terminus of the fusion protein;
(b') a translocation peptide of 34-112 amino acid residues in length, comprising an amino acid sequence that is at least 90% identical to SEQ ID NO: 3, 4, 20, or 41, located at the C-terminus of the APC-binding domain or the CD91 receptor-binding domain;
(c') an antigen of a pathogen;
(d') a nuclear export signal, comprising the amino acid sequence of SEQ ID NO: 44; and
(e') an endoplasmic reticulum retention sequence, located at the C-terminus of the fusion protein; wherein the nuclear export signal is located between the antigen and the endoplasmic reticulum retention sequence, or between the translocation peptide and the antigen.

19. The composition of claim 18:
wherein the translocation peptide is of 34-61 amino acid residues in length, comprising an amino acid sequence that is at least 90% identical to SEQ ID NO: 3, 20, or 41.

* * * * *

UNITED STATES PATENT AND TRADEMARK OFFICE
CERTIFICATE OF CORRECTION

PATENT NO. : 9,775,898 B2  
APPLICATION NO. : 15/052713  
DATED : October 3, 2017  
INVENTOR(S) : Chia-Mao Wu et al.

Page 1 of 1

It is certified that error appears in the above-identified patent and that said Letters Patent is hereby corrected as shown below:

In the Claims

Column 76, Line 48, Claim 4 delete "SEQ II)" and substitute -- SEQ ID --

Column 77, Line 9, Claim 11 delete "translocation domain" and substitute -- transduction domain --

Column 77, Line 34, Claim 13 delete "900/identical" and substitute -- 90% identical --

Signed and Sealed this
Twenty-eighth Day of November, 2017

Joseph Matal
*Performing the Functions and Duties of the
Under Secretary of Commerce for Intellectual Property and
Director of the United States Patent and Trademark Office*